(12) United States Patent
Friedrich et al.

(10) Patent No.: US 6,835,381 B1
(45) Date of Patent: Dec. 28, 2004

(54) METHODS FOR MODULATING ANGIOGENESIS BY USING THE ANTI-ANGIOGENIC ANGIOTENSIN-7 AND POLYNUCLEOTIDES ENCODING THEREFOR

(75) Inventors: Gabi Friedrich, Leverkusen (DE); Gustav Hagen, Leverkusen (DE); Maresa Wick, Berlin (DE); Dmitry Zubov, Cologne (DE); Nathalie Dubois-Stringfellow, Berkeley, CA (US)

(73) Assignee: Bayer AG, Leverkusen (DE)

( * ) Notice: Subject to any disclaimer, the term of this patent is extended or adjusted under 35 U.S.C. 154(b) by 378 days.

(21) Appl. No.: 10/018,386

(22) PCT Filed: Jun. 30, 2000

(86) PCT No.: PCT/US00/18170

§ 371 (c)(1),
(2), (4) Date: May 17, 2002

(87) PCT Pub. No.: WO01/02434

PCT Pub. Date: Jan. 11, 2001

(30) Foreign Application Priority Data

Jul. 2, 1999 (EP) ............................................. 99113502

(51) Int. Cl.[7] ........................ A61K 39/00; A61K 39/02; A01N 37/18

(52) U.S. Cl. ...................... 424/184.1; 514/2; 424/200.1
(58) Field of Search ........................... 424/184.1, 200.1; 514/2

(56) References Cited

FOREIGN PATENT DOCUMENTS

WO   WO 99/15653   4/1999

OTHER PUBLICATIONS

Maisonpierre, et al., Distinct rat genes with related profiles of expression define a TIE receptor tyrosine kinase family, Oncogene 1993, vol. 8, pp. 1631–1637.
Korhonen, et al., Enhanced expression Of the tie receptor tyrosine kinase in endothelial cells during neovascularization, Blood, vol. 80, No. 10 (Nov. 15), 1992, pp. 2548–2555.
Valenzuela, et al, Angiopoietins 3 and 4: Diverging gene counterparts in mice and humans, Proc. Natl. Acad. Sci. USA, vol. 96, Mar. 1999, pp. 1904–1909.
Partanen, et al., Putative tyrosine kinases expressed in K–562 human leukemia cells, Proc. Natl. Acad. Sci. USA, vol. 87, Nov. 1990, Cell Biology, pp. 8913–8917.

*Primary Examiner*—Gary B. Nickol
(74) *Attorney, Agent, or Firm*—John W. Mahoney

(57) ABSTRACT

The present invention provides methods for modulating angiogenesis by administering anti-angiogenic Ang-7 polypeptides to a subject. Methods of modulating angiogenesis by administering an anti-angiogenic ANG-7 nucleic acid are also provided.

27 Claims, 7 Drawing Sheets

Fig. 1

```
GAAAATGAGG CTGCTGCGGA CGGCCTGAGG ATGAACCCCA AGCCCTGGAC CTGCCGAGCG TGGCACTGAG 70
GCAGCGGCTG ACGCTACTGT GAGGGAAAGA AGGTTGTGAG CAGCCCCGCA GGACCCCTGG CCAGCCCTGG 140
CCCCAGCCTC TGCCGGAGCC CTCTGTGGAG GCAGAGCCAG TGGAGCCCAG TGAGGCAGGG CTGCTTGGCA 210
GCCACCGGCC TGCAACTCAG GAACCCCTCC AGAGGCCATG GACAGGCTGC CCCGCTGACG GCCAGGGTGA 280
AGCATGTGAG GAGCCGCCCC GGAGCCAAGC AGGAGGGAAG AGGCTTTCAT AGATTCTATT CACAAAGAAT 350
AACCACCATT TTGCAAAGAC CATGAGGCCA CTGTGCGTGA CATGCTGGTG GCTCGGACTG CTGGCTGCCA 420
TGGGAGCTGT TGCAGGCCAG GAGGACGGTT TTGAGGGCAC TGAGGAGGGC TCGCCAAGAG AGTTCATTTA 490
CCTAAACAGG TACAAGCGGG CGGGCGAGTC CCAGGACAAG TGCACCTACA CCTTCATTGT GCCCCAGCAG 560
CGGGTCACGG GTGCCATCTG CGTCAACTCC AAGGAGCCTG AGGTGCTTCT GGAGAACCGA GTGCATAAGC 630
AGGAGCTAGA GCTGCTCAAC AATGAGCTGC TCAAGCAGAA GCGGCAGATC GAGACGCTGC AGCAGCTGGT 700
GAAGGTGGAC GGCGGCATTG TGAGCGAGGT GAAGCTGCTG CGCAAGGAGA GCCGCAACAT GAACTCGCGG 770
GTCACGCAGC TCTACATGCA GCTCCTGCAC GAGATCATCC GCAAGCGGGA CAACGCGTTG GAGCTCTCCC 840
AGCTGGAGAA CAGGATCCTG AACCAGACAG CCGACATGCT GCAGCTGGCC AGCAAGTACA AGGACCTGGA 910
GCACAAGTAC CAGCACCTGG CCACACTGGC CCACAACCAA TCAGAGATCA TCGCGCAGCT TGAGGAGCAC 980
TGCCAGAGGG TGCCCTCGGC CAGGCCCGTC CCCCAGCCAC CCCCGCTGC CCCGCCCCGG GTCTACCAAC 1050
CACCCACCTA CAACCGCATC ATCAACCAGA TCTCTACCAA CGAGATCCAG AGTGACCAGA ACCTGAAGGT 1120
GCTGCCACCC CCTCTGCCCA CTATGCCCAC TCTCACCAGC CTCCCATCTT CCACCGACAA GCCGTCGGGC 1190
CCATGGAGAG ACTGCCTGCA GGCCCTGGAG GATGGCCACG ACACCAGCTC CATCTACCTG GTGAAGCCGG 1260
AGAACACCAA CCGCCTCATG CAGGTGTGGT GCGACCAGAG ACACGACCCC GGGGGCTGGA CCGTCATCCA 1330
GAGACGCCTG GATGGCTCTG TTAACTTCTT CAGGAACTGG GAGACGTACA AGCAAGGGTT TGGGAACATT 1400
GACGGCGAAT ACTGGCTGGG CCTGGAGAAC ATTTACTGGC TGACGAACCA AGGCAACTAC AAACTCCTGG 1470
TGACCATGGA GGACTGGTCC GGCCGCAAAG TCTTTGCAGA ATACGCCAGT TTCCGCCTGG AACCTGAGAG 1540
CGAGTATTAT AAGCTGCGGC TGGGGCGCTA CCATGGCAAT GCGGGTGACT CCTTTACATG GCACAACGGC 1610
AAGCAGTTCA CCACCCTGGA CAGAGATCAT GATGTCTACA CAGGAAACTG TGCCCACTAC CAGAAGGGAG 1680
GCTGGTGGTA TAACGCCTGT GCCCACTCCA ACCTCAACGG GGTCTGGTAC CGCGGGGGCC ATTACCGGAG 1750
CCGCTACCAG GACGGAGTCT ACTGGGCTGA GTTCCGAGGA GGCTCTTACT CACTCAAGAA AGTGGTGATG 1820
ATGATCCGAC CGAACCCCAA CACCTTCCAC TAAGCCAGCT CCCCCTCCTG ACCTCTCGTG GCCATTGCCA 1890
GGAGCCCACC CTGGTCACGC TGGCCACAGC ACAAAGAACA ACTCCTCACC AGTTCATCCT GAGGCTGGGA 1960
GGACCGGGAT GCTGGATTCT GTTTTCCGAA GTCACTGCAG CGGATGATGG AACTGAATCG ATACGGTGTT 2030
TTCTGTCCCT CCTACTTTCC TTCACACCAG ACAGCCCCTC ATGTCTCCAG GACAGGACAG GACTACAGAC 2100
AACTCTTTCT TTAAATAAAT TAAGTCTCTA CAATAAAAAC ACAACTGCAA AGTAAAAAAA AAAAAAAAAA 2170
AAA                                                                     2173
```

Fig. 2

```
MRPLCVTCWW LGLLAAMGAV AGQEDGFEGT EEGSPREFIY LNRYKRAGES QDKCTYTFIV PQQRVTGAIC  70
VNSKEPEVLL ENRVHKQELE LLNNELLKQK RQIETLQQLV KVDGGIVSEV KLLRKESRNM NSRVTQLYMQ 140
LLHEIIRKRD NALELSQLEN RILNQTADML QLASKYKDLE HKYQHLATLA HNQSEIIAQL EEHCQRVPSA 210
RPVPQPPPAA PPRVYQPPTY NRIINQISTN EIQSDQNLKV LPPPLPTMPT LTSLPSSTDK PSGPWRDCLQ 280
ALEDGHDTSS IYLVKPENTN RLMQVWCDQR HDPGGWTVIQ RRLDGSVNFF RNWETYKQGF GNIDGEYWLG 350
LENIYWLTNQ GNYKLLVTME DWSGRKVFAE YASFRLEPES EYYKLRLGRY HGNAGDSFTW HNGKQFTTLD 420
RDHDVYTGNC AHYQKGGWWY NACAHSNLNG VWYRGGHYRS RYQDGVYWAE FRGGSYSLKK VVMMIRPNPN 490
TFH                                                                         493
```

Fig. 3

METHODS FOR MODULATING ANGIOGENESIS BY USING THE ANTI-ANGIOGENIC ANGIOTENSIN-7 AND POLYNUCLEOTIDES ENCODING THEREFOR

BACKGROUND OF THE INVENTION

The cellular behavior responsible for the development, maintenance and repair of differentiated cells and tissues is regulated, in large part, by intercellular signals conveyed via growth factors and other ligands and their receptors. The receptors for these intracellular signaling molecules are located on the cell surface of responding cells. Growth factors and other ligands bind to the receptors, thereby causing transduction of a signal across the cell membrane. Such signal transduction can occur by many modes, including pore formation and phosphorylation. Phosphorylation of tyrosines on proteins by tyrosine kinases is one of the key modes by which signals are transduced across the cell membrane. Indeed, several currently known protein tyrosine kinase genes encode transmembrane receptors for polypeptide growth factors and hormones.

Angiogenesis is generally thought to be heavily regulated by growth factors and other ligands. Angiogenesis, and the concurrent tissue development and regeneration, depends on the tightly controlled processes of endothelial cell proliferation, migration, differentiation and survival. Both stimulator and inhibitor ligands appear to interact, directly or indirectly, with cellular receptors during these processes. Angiogenesis begins with the erosion of the basement membrane by enzymes released by endothelial cells and leukocytes. The endothelial cells, which line the lumen of blood vessels, then protrude through the basement membrane. Angiogenic stimulators induce endothelial cells to migrate through the eroded basement membrane. The migrating cells then form a "sprout" off the parent blood vessel, where the endothelial cells undergo mitosis and proliferate. The endothelial sprouts merge with each other to form capillary loops, creating the new blood vessel.

The ligands and receptors involved in endothelial cell regulation are beginning to be elucidated. In particular, endothelial growth factor receptors and their kinases have been discovered. For example, a gene encoding an endothelial cell transmembrane tyrosine kinase was described by Partanen et al. (*Proc. Natl. Acad. Sci. USA* 87:8913–17 (1990)). This gene and its encoded protein are called "TIE," which is an abbreviation for "tyrosine kinase with Ig and EGF homology domains." (See Partanen et al., *Mol. Cell. Biol.* 12:1698–1707 (1992); International Patent Publication WO 99/15653.) Enhanced TIE expression was shown during neovascularization to be associated with developing ovarian follicles and granulation tissue in skin wounds. (See Korhonen et al., *Blood* 80:2548–2555 (1992).) Thus, TIE protein is likely to play a role in angiogenesis.

Two structurally related rat TIE receptor-like tyrosine kinases, TIE-1 and TIE-2, have been reported; these receptors are encoded by distinct genes. (See Maisonpierre et al., *Oncogene* 8:1631–7 (1993).) Both genes were found to be widely expressed in endothelial cells of embryonic and postnatal tissues. Significant levels of TIE-2 transcripts were also present in other embryonic cell populations, including lens epithelium, heart epicardium and regions of mesenchyme. (See Maisonpierre et. al., supra.) The predominant expression of TIE receptors in vascular endothelia suggests that TIE plays a role in the development and maintenance of the vascular system, and in particular, angiogenesis.

Ligands of the TIE receptors have also been characterized. Two TIE-2 binding ligands, angiopoietin-1 (Ang-1) and angiopoietin-2 (Ang-2), have been identified. Ang-1 polypeptide interacts with the TIE-2 receptor tyrosine kinase. (See Maisonpierre et al., *Science* 277:55–60 (1997).) Ang-2 polypeptide is antagonistic to Ang-1 polypeptide, preventing binding of the activating ligand and blocking its ability to stimulate TIE-2 kinase activity and autophosphorylation. Ang-1 and Ang-2 do not bind TIE-1, however. Ang-1 and Ang-2 are about 60% identical; the amino acid sequences of these polypeptides share similar domain structure with an N-terminal coiled-coil region and a C-terminal fibrinogen-like domain. Northern (RNA) analysis shows that ANG-1 RNA is quite widely expressed, but that the expression of ANG-2 RNA is very limited. ANG-2 RNA is present only in tissues such as ovary, uterus, and placenta, which undergo vascular remodeling. Ang-1 is thought to be the same as the human TIE receptor ligand "htie-2" or "hTL-1." (See International Patent Publication WO 99/15653.)

Recently, other ligands for the TIE-2 receptor were identified. (See Valenzuela et al., *Proc. Natl. Acad. Sci. USA* 96:1904–09 (1999).) These ligands are called TIE ligand-3 (or angiopoietin-3 (Ang-3)) and TIE ligand-4 (or angiopoietin-4 (Ang-4)). Ang-3, a mouse polypeptide, appears to be antagonistic to Tie2 receptor while Ang-4, a human polypeptide, appears to be an agonist. The precise physiological role of Ang-3 and Ang-4 polypeptides remains to be elucidated.

Other TIE ligand homologues from humans, NL1 to NL6 and NL8, have also been identified. (See International Patent Publications WO 99/15653 and WO 99/15654.) One of these homologues, NL6, was identified by screening a cDNA library for sequences that encode secretory signals. Subsequent analysis of the full length NL6 cDNA revealed homology to TIE ligand receptors. The other homologues, NL1–5 and NL8, were identified by screening an EST database for sequences showing similarity to NL6. Based on their similarity to NL6, NL1–5 and NL8, were also proposed to be involved in angiogenesis. NL1 and NL8 were found to be capable of making cells tumorigenic. (See International Patent Publication WO 99/15653.)

The number of TIE ligand homologues, including Ang-1 to Ang-4 and the NL family, suggests that these ligands play diverse roles in angiogenesis. Further characterization of these ligands is, therefore an important step in understanding their roles in angiogenesis. In particular, persistent, unregulated angiogenesis occurs in a multiplicity of disease states, including tumor metastasis and abnormal growth by endothelial cells, and supports the pathological damage seen in these conditions. Thus, characterization of angiogenic factors may also facilitate the development of treatments for diseases related to (and hypothesized as being related to) angiogenesis. For example, tumor formation has been proposed to be dependent on angiogenesis. Thus, TIE ligand homologues that inhibit angiogenesis may provide therapeutic treatments for such tumors.

SUMMARY OF THE INVENTION

The present invention provides methods for modulating angiogenesis using anti-angiogenic Ang-7 polypeptides. The present invention further encompasses the use of Ang-7 polypeptides for the treatment of a disease or clinical condition where angiogenesis is relevant to the causation or treatment of the disease or clinical condition. In one embodiment, such diseases or conditions include, but are not limited to, cancer, wound healing, tumor formation, diabetic retinopathies, macular degeneration, cardiovascular diseases, and the like. Further uses of the Ang-7 polypeptides include treatment of clinical conditions involving angiogenesis in the reproductive system, including regulation of placental vascularization or use as an abortifacient. The present invention also encompasses pharmaceutical compositions containing the Ang-7 polypeptide and the use of such pharmaceutical compositions for the treatment of the above-mentioned diseases or clinical conditions.

One aspect of the present invention relates to the use of Ang-7 polypeptides having the amino acid sequence of SEQ ID NO:2, as well as biologically active or diagnostically or therapeutically useful fragments, variants, derivatives and analogs thereof. An additional aspect relates to the use of antibodies against the Ang-7 polypeptides of the present invention, especially antibodies which bind specifically to an epitope of the sequence described in SEQ ID NO:2, or a sequence that shares at least 60%, preferably at least 70%, more preferably at least 80%, still more preferably at least 90%, or most preferably at least 95% sequence identity over at least 20, preferably at least 30, more preferably at least 40, still more preferably at least 50, or most preferably at least 100 residues, to SEQ ID NO:2.

Another aspect of the present invention relates to the use of isolated ANG-7 nucleic acids encoding the Ang-7 polypeptides of the present invention, including mRNAs, DNAs, cDNAs, genomic DNA, as well as ANG-7 antisense nucleic acids. Such nucleic acids include the ANG-7 cDNA sequence having the nucleotide sequence of SEQ ID NO: 1. Another aspect relates to ANG-7 sequence fragments or variants that encode biologically active or diagnostically or therapeutically useful polypeptides. Such fragments or variants include sequences having all possible codon choices for the same amino acid or conservative amino acid substitutions thereof, such as the nucleotide sequence identified as NL1 in International Patent Publication WO 99/15653 (SEQ ID NO: 1), the disclosure of which is incorporated in its entirety by reference herein. Other variants include those nucleic acids that are capable of selectively hybridizing to a human ANG-7 cDNA (e.g., SEQ ID NO:1) under stringent hybridization conditions. Another aspect of the present invention relates to nucleic acid probes comprising polynucleotides of sufficient length to selectively hybridize to a polynucleotide encoding an Ang-7 polypeptide of the present invention.

Still another aspect of the present invention relates to processes for producing Ang-7 polypeptides, or biologically active and diagnostically or therapeutically useful fragments or variants thereof, by recombinant techniques through the use of recombinant vectors. A further aspect of the present invention relates to recombinant prokaryotic and/or eukaryotic host cells comprising an ANG-7 nucleic acid sequence encoding an Ang-7 polypeptide, or biologically active or diagnostically or therapeutically useful fragments or variants thereof. In a related aspect, nucleic acid constructs are provided that express ANG-7 nucleic acids and/or Ang-7 polypeptides, fragments or variants. Such constructs typically include a transcriptional promoter and a transcriptional terminator, each operably linked for expression of the ANG-7 nucleic acid or fragment thereof.

Another aspect of the present invention relates to processes involving expression of the polypeptides, or polynucleotides encoding the polypeptides, of the present invention for purposes of gene therapy. As used herein, gene therapy is defined as the process of providing for the expression of nucleic acid sequences of exogenous origin in an individual for the treatment of a disease condition within that individual.

A further aspect of the present invention relates to processes for utilizing Ang-7 polypeptides fragments, variants, derivatives, or analogs thereof, or ANG-7 polynucleotides or fragments, variants or derivatives thereof, for therapeutic purposes involving the modulation of angiogenesis, or the modulation of diseases or conditions in which angiogenesis is relevant to the disease or condition. Such diseases or conditions include, for example, the treatment of cancer, wound healing, diabetic retinopathies, macular degeneration, cardiovascular diseases, and clinical conditions involving angiogenesis in the reproductive system, including regulation of placental vascularization or use as an abortifacient. Such treatments further include the use of the Ang-7 polypeptides in protein replacement therapy and protein mimetics.

Another aspect of the present invention relates to diagnostic assays for detecting diseases or clinical conditions, or the susceptibility to diseases or clinical conditions, related to mutations in an ANG-7 nucleic acid sequence of the present invention and for detecting over-expression or underexpression of Ang-7 polypeptides encoded by such sequences.

These and other aspects of the invention will become evident upon reference to the following description and drawings.

BRIEF DESCRIPTION OF THE DRAWINGS

FIG. 1 depicts the nucleotide sequence of ANG-7 cDNA.

FIG. 2 depicts the amino-acid sequence of human Ang-7 polypeptide. The sequence is shown in the one letter code of amino-acids.

FIG. 3 depicts an alignment of the Ang-7 (SEQ ID NO:2) amino acid sequence with those of Ang-1 (SEQ ID NO:3), Ang-2 (SEQ ID NO:4), Ang-3 (SEQ ID NO:5), and Ang-4 (SEQ ID NO:6). Identical amino acids are indicated by boxes.

| | | |
|---|---|---|
| 1-whole brain | 28-interventricular | 56-liver |
| 2-cerebral cortex | septum | 57-pancreas |
| 3-frontal lobe | 29-apex of the heart | 58-adrenal gland |
| 4-parietal lobe | 30-esophagus | 59-thyroid gland |
| 5-occipital lobe | 31-stomach | 60-salivary gland |
| 6-temporal lobe | 32-duodenum | 61-mammary gland |
| 7-paracentral gyrus of | 33-jejunum | 62-Leukemia HL-60 |
| cerebral complex | 34-ileum | 63-HeLa S3 |
| 8-pons | 35-ilocecum | 64-Leukemia K-562 |
| 9-cerebellum left | 36-appendix | 65-Leukemia MOLT-4 |
| 10-cerebellum right | 37-colon ascending | 66-Burkitt's lymphoma, |
| 11-corpus callusum | 38-colon transverse | Raji |
| 12-amygdala | 39-rectum | 67-Burkitt's |
| 13-caudate nucleus | 40-kidney | lymphoma, |
| 14-hippocalamus | 41-skeletal muscle | Daudi |
| 15-medulla oblongata | 42-spleen | 68-colorect. adenocarc. |
| 16-putamen | 43-thymus | SW-480 |
| 17-subtantia nigra | 44-peripheral blood | 69-Lung carcinoma |
| 18-accumbens nucleus | 45-lymph node | A549 |
| 19-thalamus | 46-bone marrow | 70-fetal brain |
| 20-pituitary gland | 47-trachea | 71-fetal heart |
| 21-spinal cord | 48-lung | 72-fetal kidney |
| 22-heart | 50-placenta | 73-fetal liver |
| 23-aorta | 51-bladder | 74-fetal spleen |
| 24-atrium left | 52-uterus | 75-fetal thymus |
| 25-atrium right | 53-prostate | 76-fetal lung |
| 26-ventricle left | 54-testis | |
| 27-ventricle right | 55-ovary | |

Figure 5:
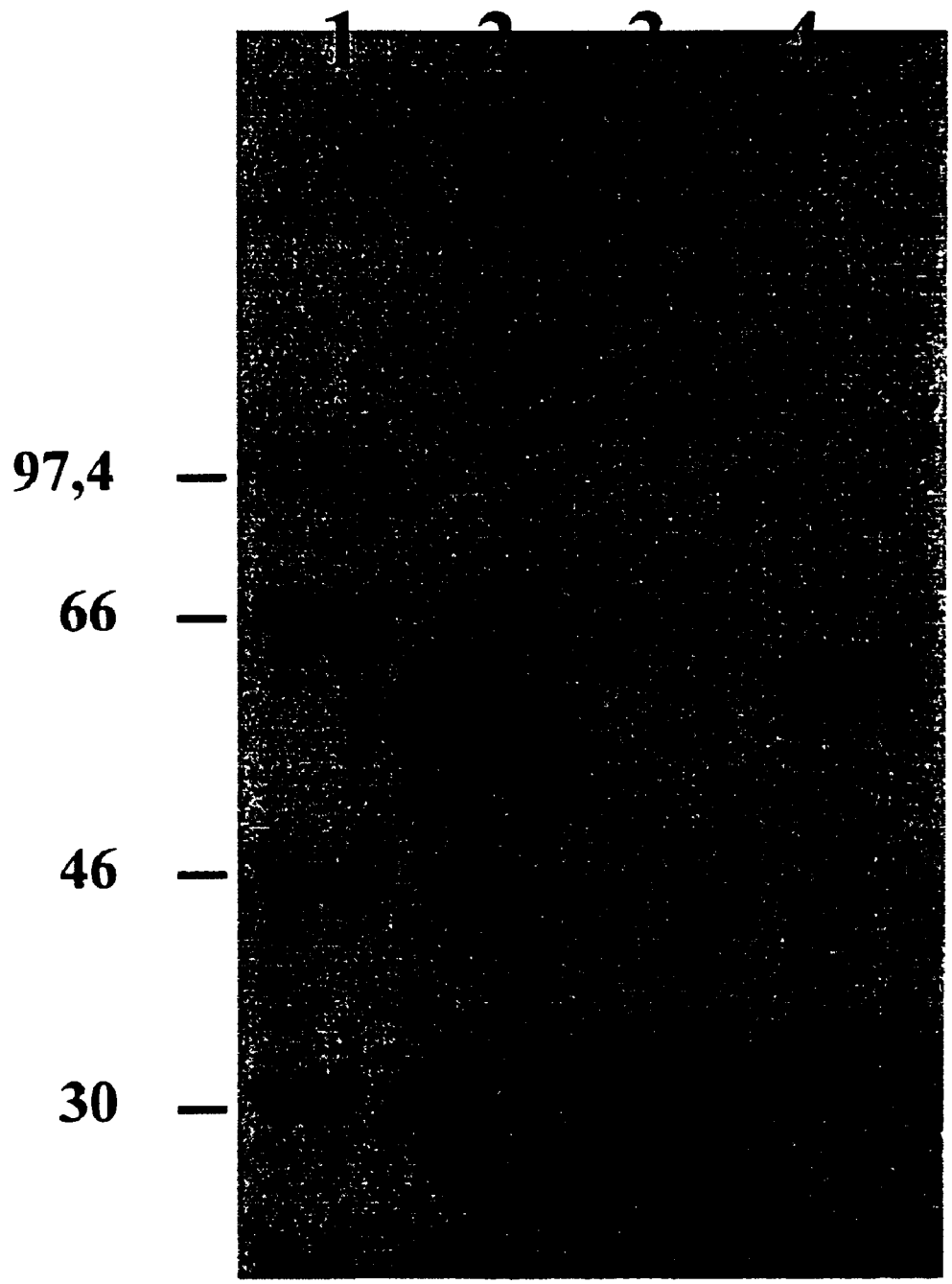

FIG. 5 depicts the results of the in vitro translation of Ang-7 RNA. Lane 1: Rainbow [$^{14}$C]methylated protein molecular weight markers (Amersham, Little Chalfont Buckinghamshire, England) containing the following proteins: ovalbumin (46 kDa), carbonic anhydrase (30 kDa), tsypsin inhibitor (21.5 kDa), lysozyme (14.3 kDa), and aprotinin (6.5 kDa). Lane 2: In vitro translation products of ANG-7 RNA using the T7 promoter of the mammalian expression vector pcDNA3.1/Myc-His(−) (Invitrogen, Groningen, Netherlands). Lane 3: In vitro translation products of RNA using the SP6 promoter of the mammalian expression vector pcDNA3.1/Myc-His(−) (negative control). Lane 4: Positive control from the in vitro translation system (Promega, Madison, USA).

Figure 6:
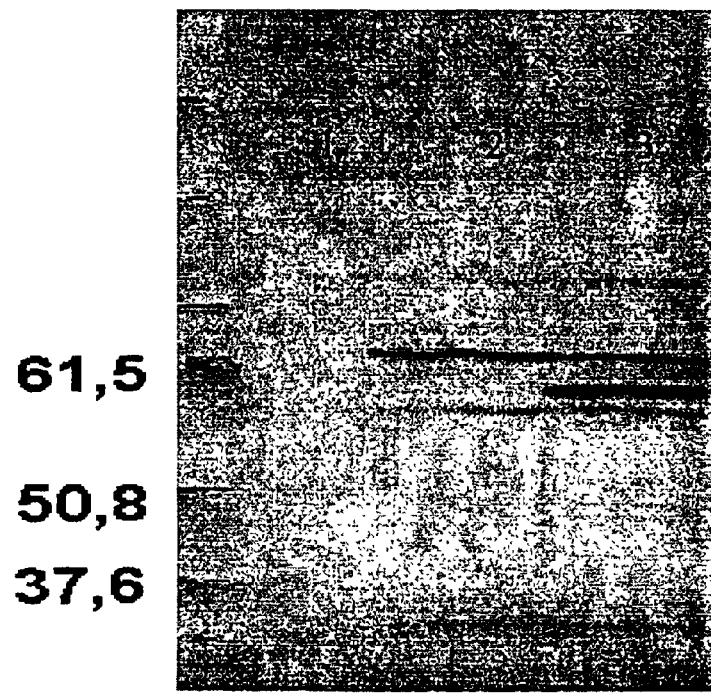

FIG. 6 depicts Western blot analysis of the cell extract of CHO cells transiently transfected with an ANG-7 expression construct. Lane 1: protein molecular weight markers. Lane 2: CHO cells (negative control). Lane 3: transiently transfected CHO cells expressing Ang-7 polypeptide. The Ang-7 polypeptide band is marked by an arrow.

Figure 7:
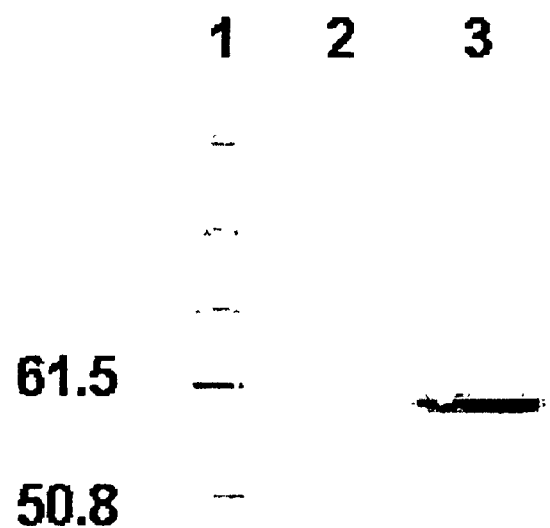

FIG. 7 depicts a Western blot analysis of Ang-7 polypeptide in the cell lysate of a stably transfected HEK293 cell clone. Lane 1: protein molecular weight markers. Lane 2: cell lysate from HEK293 cells (negative control). Lane 3: cell lysate from stably transfected HEK293 cells expressing Ang-7 polypeptide.

Figure 8:

FIG. 8 depicts a Western blot analysis of conditioned media from a stably transfected HEK293 cell clone expressing Ang-7 polypeptide. Lane 1: conditioned media from HEK293 cells (negative control). Lane 2: conditioned media from the stably transfected HEK293 cell clone expressing Ang-7 polypeptide.

Figure 9:
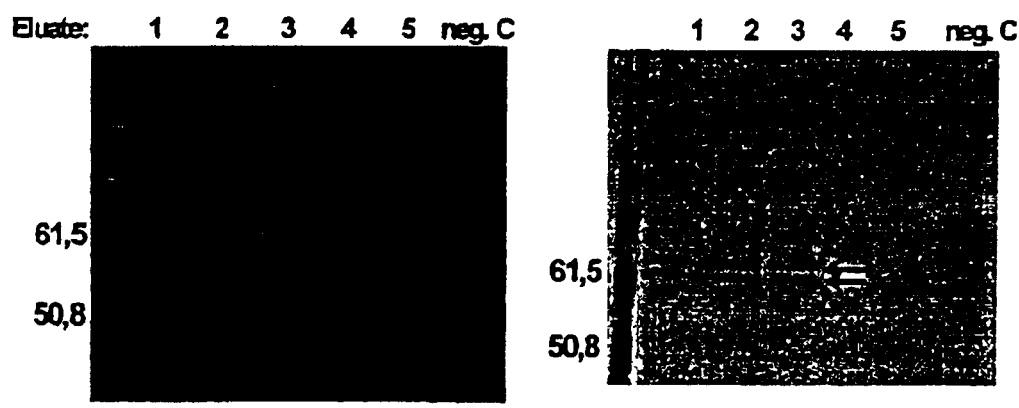

FIGS. 9A and 9B depict the results of purification of Ang-7 polypeptide from conditioned media. FIG. 9A: Western blot analysis; FIG. 9B: coomassie-stained SDS gel of purified Ang-7 polypeptide. The arrows in FIG. 9B indicate the position of recombinant Ang-7 polypeptide. For each figure, Lanes 1–5 are fractions 1–5 eluted from the Ni-NTA agarose column. Lane "neg. C" indicates the negative control (conditioned media from HEK293 cells). In FIG. 9B, the double bands probably represent different glycosylation forms of Ang-7 polypeptide.

DETAILED DESCRIPTION

Prior to setting forth the invention in more detail, it may be helpful to a further understanding thereof to set forth definitions of certain terms as used hereinafter.

Definitions:

Unless defined otherwise, all technical and scientific terms used herein have the same meaning as commonly understood by one of ordinary skill in the art to which this invention belongs. Other methods and materials similar to those described herein can be used in the practice or testing of the present invention; thus, only exemplary methods and materials are described. For purposes of the present invention, the following terms are defined below.

The term "angiogenesis" means the generation of new blood vessels in a tissue or organ. Angiogenesis includes neovascularization and collateral vascularization. "Normal angiogenesis" includes, under normal physiological conditions, new blood vessel formation associated with wound healing, fetal and embryonal development and formation of the corpus luteum, endometrium and placenta. "Unwanted angiogenesis" refers to angiogenesis that occurs under abnormal physiological conditions, such as in a disease or clinical condition associated with pathological damage related to the uncontrolled angiogenesis. For example, unwanted angiogenesis can occur during tumor formation, where neovascularization is present within the tumor.

The term "ANG-7 nucleic acids" (ie., in all caps and italicized) refers to polynucleotides encoding Ang-7 polypeptides, including mRNAs, DNAs, cDNAs, genomic DNA, as well as antisense nucleic acids, and polynucleotides encoding biologically active or diagnostically or therapeutically useful fragments, variants and derivatives thereof. Useful fragments and variants include those based on all possible codon choices for the same amino acid, and codon choices based on conservative amino acid substitutions, and biologically active or diagnostically or therapeutically useful fragments, or derivatives thereof. Useful variants further include those having at least 70% polynucleotide sequence identity, more preferably 80%, still preferably 90%, to the polynucleotide of SEQ ID NO:1, and biologically active and diagnostically or therapeutically useful fragments, or derivatives thereof.

The term "ANG-7 gene" (ie, in all caps and italicized) refers to coding sequences, intervening sequences and regulatory elements controlling transcription and/or translation.

The terms "polynucleotide" and "nucleic acid" refer to a polymer composed of a multiplicity of nucleotide units (ribonucleotide or deoxyribonucleotide or related structural variants), which are typically linked via phosphodiester bonds. A polynucleotide or nucleic acid can be of substantially any length, typically from about six (6) nucleotides to about $10^9$ nucleotides or larger. Polynucleotides or nucleic acids include RNA, cDNA, genomic DNA, synthetic forms, and mixed polymers, both sense and antisense strands, and can also be chemically or biochemically modified or can contain non-natural or derivatized nucleotide bases, as will be readily appreciated by the skilled artisan. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, and the like), charged linkages (e.g., phosphorothioates, phosphorodithioates, and the like), pendent moieties (e.g., polypeptides), intercalators (e.g., acridine, psoralen, and the like), chelators, alkylators, and modified linkages (e.g., alpha anomeric nucleic acids, and the like). Also included are synthetic molecules that mimic polynucleotides in their ability to bind to a designated nucleotide sequence via hydrogen bonding and other chemical interactions. Such molecules are known in the art and include, for example, those in which peptide linkages substitute for phosphate linkages in the backbone of the molecule.

The term "oligonucleotide" refers to a polynucleotide of from about six (6) to about one hundred (I 00) nucleotides, or more in length. Thus, oligonucleotides are a subset of polynucleotides. Oligonucleotides can be synthesized on an automated oligonucleotide synthesizer (e.g., those manufactured by Applied BioSystems (Foster City, Calif.)), according to specifications provided by the manufacturer.

The term "primer" refers to a polynucleotide, typically an oligonucleotide, whether occurring naturally, as in an enzyme digest, or produced synthetically in vitro, which acts as a point of initiation of polynucleotide synthesis when used under conditions in which a primer extension product is synthesized.

The term "Ang-7 polypeptide" refers to polypeptides having the amino acid sequence of SEQ ID NO:2, and biologically active or diagnostically or therapeutically useful fragments, variants and derivatives thereof. "Fragment" refers to a portion of an Ang-7 polypeptide having typically at least 10 contiguous amino acids, more typically at least 20, still more typically at least 50 contiguous amino acids of the Ang-7 polypeptide. Useful variants typically include those having conservative amino acid substitutions, and biologically active and diagnostically or therapeutically useful fragments thereof. Useful variants are typically at least about 50% similar to the native Ang-7 amino acid sequence (SEQ ID NO:2), more typically in excess of about 90%, and still more typically at least about 95% similar, and biologically active, or diagnostically or therapeutically useful fragments or derivatives thereof. Ang-7 polypeptides further include those that are immunologically cross-reactive with anti-Ang-7 polypeptides The term "polypeptide" refers to a polymer of amino acids and its equivalent and does not refer to a specific length of the product; thus, peptides and oligopeptides (i.e., fragments) and proteins are included within the definition of a polypeptide. This term also includes derivatives of the Ang-7 polypeptide, for example, glycosylations, acetylations, phosphorylations, and the like. Included within the definition are, for example, polypeptides containing one or more analogs of an amino acid (e.g., unnatural amino acids, and the like), polypeptides with substituted linkages as well as other modifications known in the art, both naturally and non-naturally occurring.

The term "biologically active" refers to the ability of a molecule to modulate angiogenesis, such as by affecting endothelial tube formation (e.g., using the HUVEC assay of Example 9 (infra)), or that affects tumor cell growth or proliferation (e.g., using the tumor cell growth inhibition assay of Example 10 (infra)). Biologically active molecules can be Ang-7 polypeptides, fragments, variants, derivatives and analogs thereof; nucleic acids encoding Ang-7 polypeptides, fragments, variants and derivatives thereof; and anti-Ang-7 antibodies, which modulate angiogenesis (e.g., inhibiting or stimulating endothelial tube formation) or by modulating tumor cell growth or proliferation (e.g., inhibiting or stimulating tumor cell growth).

The terms "therapeutically useful" or "therapeutically effective" refer to an amount of a molecule (e.g., an Ang-7 polypeptide, anti-Ang-7 antibody, or ANG-7 nucleic acid) that is sufficient to modulate angiogenesis (e.g. inhibiting or stimulating endothelial tube formation) or to modulate tumor cell growth or proliferation (e.g., inhibiting or stimulating tumor cell growth) in a subject, such as a patient or a mammal.

The terms "diagnostically useful" or "diagnostically effective" refer to a molecule (e.g., an Ang-7 polypeptide, anti-Ang-7 antibody, or ANG-7 nucleic acid) for detecting angiogenesis, or the inhibition of angiogenesis, in a subject. These terms further include molecules useful for detecting diseases or clinical conditions, or the susceptibility to diseases or clinical conditions, related to mutations in an ANG-7 nucleic acid sequence of the present invention and for detecting over-expression or underexpression of Ang-7 polypeptides encoded by such sequences.

The term "Ang-7 compounds" or "Ang-7 anti-angiogenic compounds" refers to biologically active Ang-7 polypeptide, fragments, variants, derivatives, or analogs thereof, to anti-Ang-7 antibodies, to biologically active ANG-7 nucleic acids, fragments or derivatives, and to ANG-7 antisense nucleic acids.

The terms "amino acid," "amino acid residue," or "residue" refer to naturally occurring L amino acids or to D amino acids as described further below. Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes. (See, e.g., Bruce Alberts et al., *Molecular Biology of the Cell*, Garland Publishing, Inc., New York (3d ed. 1994)).

The terms "identical" or "percent identity," in the context of two or more nucleic acids or polypeptide sequences, refer to two or more sequences or subsequences that are the same or have a specified percentage of nucleotides or amino acids that are the same, when compared and aligned for maximum correspondence, as measured using one of the following sequence comparison algorithms, or by visual inspection.

The term "substantially identical," in the context of two nucleic acids, or two polypeptide sequences, refers to two or more sequences or subsequences that have at least 60%, typically 80%, most typically 90–95% identity, when compared and aligned for maximum correspondence, as measured using one of the sequence comparison algorithms described below, or by visual inspection. An indication that two polypeptide sequences are "substantially identical" is that one polypeptide is immunologically reactive with antibodies raised against the second polypeptide.

"Similarity" or "percent similarity" in the context of two or polypeptide sequences, refer to two or more sequences or subsequences that are the same or have a specified percentage of amino acid residues or conservative substitutions thereof, that are the same, when compared and aligned for maximum correspondence, as measured using one of the following sequence comparison algorithms, or by visual inspection. By way of example, a first protein region can be considered similar to a region of human Ang-7 polypeptide when the amino acid sequence of the first region is at least 30%, 40%, 50%, 60%, 70%, 75%, 80%, 90%, or even 95% identical, or conservatively substituted, to a region of Ang-7 polypeptide when compared to any sequence in Ang-7 polypeptide of an equal number of amino acids as the number contained in the first region, or when compared to an aligned sequence of Ang-7 polypeptide that has been aligned by a computer similarity program known in the art, as discussed above.

The term "substantial similarity" in the context of polypeptide sequences, indicates that the polypeptide comprises a sequence with at least 70% sequence identity to a reference sequence, or preferably 80%, or more preferably 85% sequence identity to the reference sequence, or most preferably 90% identity over a comparison window of about 10–20 amino acid residues. In the context of amino acid sequences, "substantial similarity" further includes conservative substitutions of amino acids. Thus, a polypeptide is substantially similar to a second polypeptide, for example, where the two peptides differ only by one or more conservative substitutions.

The term "conservative substitution," when describing a polypeptide, refers to a change in the amino acid composition of the polypeptide that does not substantially alter the polypeptide's activity. Thus, a "conservative substitution" of a particular amino acid sequence refers to amino acid substitutions of those amino acids that are not critical for protein activity or substitution of amino acids with other amino acids having similar properties (e.g., acidic, basic, positively or negatively charged, polar or non-polar, etc.) such that the substitutions of even critical amino acids do not substantially alter activity. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(See also Creighton, *Proteins*, W. H. Freeman and Company (1984).) In addition, individual substitutions, deletions or additions that alter, add or delete a single amino acid or a small percentage of amino acids in an encoded sequence are also "conservative substitutions."

For sequence comparison, typically one sequence acts as a reference sequence, to which test sequences are compared. When using a sequence comparison algorithm, test and reference sequences are input into a computer, coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith & Waterman (*Adv. Appl. Math.* 2:482 (1981)), by the homology alignment algorithm of Needleman & Wunsch (*J. Mol. Biol.* 48:443 (1970)), by the search for similarity method of Pearson & Lipman (*Proc. Natl. Acad. Sci. USA* 85:2444 (1988)), by computerized implementations of these algorithms (g., GAP, BESTFIT, FASTA, and TFASTA in the Wisconsin Genetics Software Package, Genetics Computer Group, 575 Science Dr., Madison, Wis.), or by visual inspection. (See generally Ausubel et al., *Current Protocols in Molecular Biology*, John Wiley and Sons, New York (1996).)

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng & Doolittle (*J. Mol. Evol.* 35:351–360 (1987)). The method used is similar to the method described by Higgins & Sharp (*CABIOS* 5:151–153 (1989)). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps. Another useful program for the multiple alignment of sequences is MEGALIGN™ Expert Sequence Analysis Software (DNASTAR, Madison, Wis.).

Another example of an algorithm that is suitable for determining percent sequence identity and similarity is the BLAST algorithm, which is described by Altschul et al. (*J. Mol. Biol.* 215:403–410 (1990)). (See also Zhang et al., *Nucleic Acid Res.* 26:3986–90 (1998); Altschul et al., *Nucleic Acid Res.* 25:3389–402 (1997). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (See Henikoff & Henikoff, *Proc. Natl. Acad. Sci. USA* 89:10915–9 (1992)), alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin & Altschul, *Proc. Natl. Acad. Sci. USA* 90:5873–77 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two polypeptides differ only by conservative substitutions.

The terms "transformation" or "transfection" means the process of stably altering the genotype of a recipient cell or microorganism by the introduction of polynucleotides. This is typically detected by a change in the phenotype of the recipient cell or organism. The term "transformation" is generally applied to microorganisms, while "transfection" is used to describe this process in cells derived from multicellular organisms.

Methodologies for polymerase chain reaction ("PCR") are generally disclosed in U.S. Pat. Nos. 4,683,202, 4,683,195 and 4,800,159. Other nomenclature used herein and many of the laboratory procedures in cell culture, molecular genetics and nucleic acid chemistry and hybridization, which are described below, are those well known and commonly employed in the art. (See generally Ausubel et al., *Current Protocols in Molecular Biology*, John Wiley and Sons, New York (1996); Sambrook et al., *Molecular Cloning: A Laboratory Manual*, Second Edition, Cold Spring Harbor Laboratory Press, New York (1989)). Standard techniques are used for recombinant nucleic acid methods, polynucleotide synthesis, preparation of biological samples, preparation of cDNA fragments, isolation of mRNA and the like. Generally enzymatic reactions and purification steps are performed according to the manufacturers' specifications.

The present invention provides methods for modulating angiogenesis using anti-angiogenic Ang-7 polypeptides and biologically active or diagnostically or therapeutically useful fragments, variants, derivatives or analogs thereof. The present invention further encompasses methods of using ANG-7 nucleic acids, as more fully described below, to modulate angiogenesis. The present invention further encompasses the use of Ang-7 polypeptides and/or ANG-7 nucleic acids for the treatment of a disease or clinical condition where angiogenesis is relevant to the causation or treatment of the disease or clinical condition, including but not limited to cancer, wound healing, tumor formation, diabetic retinopathies, macular degeneration, cardiovascular diseases, and the like.

ANG-7 Nucleic Acids:

One aspect of the present invention relates to isolated nucleic acids encoding Ang-7 polypeptides, including mRNAs, DNAs, cDNAs, genomic DNA, as well as antisense nucleic acids, and their use in modulating angiogenesis. ANG-7 nucleic acids include the ANG-7 cDNA sequence (e.g., SEQ ID NO: 1). ANG-7 nucleic acids further include biologically active sequence variants, such as those encoding all possible codon choices for the same amino acid or conservative amino acid substitutions thereof, and also include diagnostically or therapeutically useful fragments thereof. Such variants include the NL1 cDNA sequence (SEQ ID NO: 1 of International Patent Publication WO 99/15653).

The invention further provides purified ANG-7 nucleic acids comprising at least 6 contiguous nucleotides (e.g., a hybridizable portion) encoding a fragment of an Ang-7 polypeptide. In another embodiment, the ANG-7 nucleic acids consist of fragments of at least 8 (contiguous) nucleotides, 25 nucleotides, 50 nucleotides, 100 nucleotides, 150 nucleotides, 200 nucleotides, or even up to 250 nucleotides or more of an ANG-7 sequence. In another embodiment, the nucleic acids are larger than 200 or 250 nucleotides in length. The nucleic acids can be single- or double-stranded. As is readily apparent, as used herein, a "nucleic acid encoding a fragment of an Ang-7 polypeptide" is construed as referring to a nucleic acid encoding only the recited fragment or portion of the Ang-7 polypeptide and not the other contiguous portions of the Ang-7 polypeptide as a continuous sequence. Fragments of ANG-7 nucleic acids encoding one or more Ang-7 domains are provided.

The invention also relates to nucleic acids hybridizable to, or complementary to, the foregoing sequences, Such nucleic acids include mRNAs, DNAs, cDNAs, genomic DNA, as well as antisense nucleic acids, and biologically active and diagnostically or therapeutically useful fragments or variants thereof. Nucleic acids are also provided which comprise a sequence complementary to at least 10, 25, 50, 100, 200, or 250 nucleotides or more of an ANG-7 gene or cDNA. In one embodiment, a nucleic acid is hybridizable to an ANG-7 nucleic acid (e.g., having sequence SEQ ID NO: 1), or to a nucleic acid encoding an ANG-7 variant, under conditions of high stringency is provided.

By way of example, and not limitation, procedures using conditions of high stringency are as follows: Prehybridization of filters containing DNA is carried out for 8 hours to overnight at 65° C. in buffer composed of 6×SSC, 50 mM Tris-HCl (pH 7.5), 1 mM EDTA, 0.02% PVP, 0.02% Ficoll, 0.02% BSA, and 500 (µg/ml denatured salmon sperm DNA). Filters are hybridized for 48 hours at 65° C. in prehybridization mixture containing 100 µg/ml denatured salmon sperm DNA and 5–20×10$^6$ cpm of $^{32}$P-labeled probe. Washing of filters is done at 37° C. for 1 hour in a solution containing 2×SSC, 0.01% PVP, 0.01% Ficoll, and 0.01% BSA. This is followed by a wash in 0.1×SSC at 50° C. for 45 min before autoradiography. Other conditions of high stringency, which can be used, are well known in the art. (See generally Ausubel et al., supra).

In another embodiment, a nucleic acid which is hybridizable to an ANG-7 nucleic acid under conditions of moderate stringency is provided. By way of example, and not limitation, procedures using such conditions of moderate stringency are as follows: Prehybridization of filters containing DNA is carried out for 8 hours to overnight at 55° C. in buffer composed of 6×SSC, 50 mM Tris-HCl (pH 7.5), 1 mM EDTA, 0.02% PVP, 0.2% Ficoll, 0.02% BSA and 500 µg/ml denatured salmon sperm DNA. Filters are hybridized for 24 hours at 55° C. in a prehybridization mixture containing 100 µg/ml denatured salmon sperm DNA and 5–20× 10$^6$ cpm of $^{32}$P-labeled probe. Washing of filters is done at 37° C. for 1 hour in a solution containing 2×SSC, 0.01% PVP, 0.01% Ficoll, and 0.01% BSA.

In another embodiment, a nucleic acid which is hybridizable to an ANG-7 nucleic acid under conditions of low stringency is provided. By way of example, and not limitation, procedures using such conditions of low stringency are as follows: Filters containing DNA are pretreated for 6 hours at 40° C. in a solution containing 35% formamide, 5×SSC, 50 mM Tris-HCl (pH 7.5), 5 mM EDTA, 0.1% polyvinylpyrrolidone (PVP), 0.1% Ficoll, 1% bovine serum albumin (BSA), and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe. Filters are incubated in hybridization mixture for 18–20 hours at 40° C., and then washed for 1.5 hours at 55° C. in a solution containing 2×SSC, 25 mM Tris-HCl (pH 7.4), 5 mM EDTA, and 0.1% SDS. The wash solution is replaced with fresh solution and incubated an additional 1.5 hours. Filters are blotted dry and exposed for autoradiography. Other conditions of low stringency that can be used are well known in the art (those employed for cross-species hybridizations). (See also Shilo and Weinberg, *Proc. Natl. Acad. Sci. USA* 78:6789–6792 (1981)).

Low, moderate and high stringency conditions are well known to those of skill in the art, and will vary predictably depending on the base composition of the particular nucleic acid sequence and on the specific organism from which the nucleic acid sequence is derived. For guidance regarding such conditions see, for example, Sambrook et al., *Molecular Cloning, A Laboratory Manual* (Second Edition, Cold Spring Harbor Press, NY, pp. 9.47–9.57 (1989)); and Ausubel et al., *Current Protocols in Molecular Biology* (Green Publishing Associates and Wiley Interscience, NY (1989)).

Specific embodiments for the cloning of an ANG-7 nucleic acid, presented as a particular example but not by way of limitation, are as follows.

For expression cloning (a technique commonly known in the art), an expression library is constructed by methods known in the art. For example, mRNA (e.g., human) is isolated, cDNA is prepared and then ligated into an expression vector (e.g., a bacteriophage derivative) such that it is capable of being expressed by the host cell into which it is then introduced. Various screening assays can then be used to select for the expressed Ang-7 polypeptide. In one embodiment, anti-Ang-7 specific antibodies can be used for selection.

In another embodiment, polymerase chain reaction (PCR) is used to amplify the desired sequence in a genomic or cDNA library prior to selection. Oligonucleotides representing known ANG-7 sequences, for example, as selected from SEQ ID NO: 1, can be used as primers in PCR. In a typical embodiment, the oligonucleotide represents at least part of the ANG-7 conserved segments of sequence identity between ANG-7 of different species. The synthetic oligonucleotides can be utilized as primers to amplify particular sequences within an ANG-7 gene by PCR using nucleic acids from a source (RNA or DNA), typically a cDNA library, of potential interest. PCR can be carried out, for example, by use of a Perkin-Elmer Cetus thermal cycler and Taq polymerase (Gene Amp). The DNA being amplified can include mRNA or cDNA or genomic DNA from any eukaryotic species. One of skill in the art can choose to synthesize several different degenerate primers for use in the PCR reactions.

It is also possible to vary the stringency of hybridization conditions used in priming the PCR reactions, to allow for greater or lesser degrees of nucleotide sequence similarity between the known ANG-7 sequence and the related nucleic acid being isolated. For cross species hybridization, low stringency conditions are typically used. For same species hybridization, moderately stringent conditions are more typically used. After successful amplification of a segment of a related ANG-7 nucleic acid, that segment can be molecularly cloned and sequenced, and utilized as a probe to isolate a complete cDNA or genomic clone. This, in turn, can permit the determination of a complete nucleotide sequence, the analysis of its expression, and the production of its protein product for functional analysis, as described infra. In this fashion, additional nucleic acids encoding Ang-7 polypeptides and Ang-7 polypeptide variants can be identified.

The above-methods are not meant to limit the following general description of methods by which ANG-7 nucleic acids can be obtained. Any eukaryotic cell potentially can serve as the nucleic acid source for the molecular cloning of ANG-7 nucleic acids. The nucleic acids encoding Ang-7 polypeptide can be isolated from vertebrate sources including, mammalian sources such as, porcine, bovine, feline, avian, equine, canine and human as well as additional primate sources. The DNA can be obtained by standard procedures known in the art from cloned DNA (e.g., a DNA "library"), by chemical synthesis, by cDNA cloning, or by the cloning of genomic DNA, or fragments thereof, purified from the desired cell. (See e.g., Sambrook et al., *Molecular Cloning, A Laboratory Manual*, Second Edition, Cold Spring Harbor Laboratory Press, Cold Spring Harbor, N.Y. (1989); Glover, (ed.), *DNA Cloning: A Practical Approach*, MRL Press, Ltd., Oxford, U.K. Vol. I, II. (1985)). Clones derived from genomic DNA can contain regulatory and intron DNA regions in addition to coding regions; clones derived from cDNA will typically contain only exon sequences. Whatever the source, the nucleic acid can be molecularly cloned into a suitable vector for propagation of the nucleic acid.

In the molecular cloning of ANG-7 nucleic acids from genomic DNA, DNA fragments are generated, some of which will encode an ANG-7 gene. The DNA can be cleaved at specific sites using various restriction enzymes. Alternatively, one can use DNase in the presence of manganese to fragment the DNA, or the DNA can be physically sheared, such as, for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene can be accomplished in a number of ways. For example, a portion of an ANG-7 gene, cDNA (of any species) or its specific RNA, or a fragment thereof, can be purified and labeled, the generated DNA fragments can be screened by nucleic acid hybridization to the labeled probe (see, e.g., Benton and Davis, *Science* 196:180 (1975); Grunstein and Hogness, *Proc. Natl. Acad. Sci. USA* 72:3961 (1975)). Those DNA fragments with substantial identity to the probe will hybridize. It is also possible to identify the appropriate fragment by restriction enzyme digestion(s) and comparison of fragment sizes with those expected according to a known restriction map, if available. Further selection can be carried out on the basis of the properties of the gene.

Alternatively, the presence of the gene can be detected by assays based on the physical, chemical, or immunological properties of its expressed product. For example, cDNA clones, or DNA clones which hybrid-select the proper mRNAs, can be selected which produce a polypeptide that, for example, has similar or identical electrophoretic migration, isoelectric focusing behavior, proteolytic digestion maps, modulation of angiogenesis, receptor binding activity, or antigenic properties as known for Ang-7 polypeptide. Immune serum or an antibody which specifically binds to the Ang-7 polypeptide can be used to identify putatively Ang-7 polypeptide synthesizing clones by binding in an ELISA (enzyme-linked immunosorbent assay)-type procedure.

ANG-7 nucleic acids can also be identified by mRNA selection by nucleic acid hybridization followed by in vitro translation. In this procedure, fragments are used to isolate complementary mRNAs by hybridization. Such DNA fragments typically represent available, purified DNA of another species (e.g., human, mouse, and the like). Immunoprecipitation analyses or functional assays (e.g., inhibition of angiogenesis, endothelial tube formation in vitro tumor inhibition, or binding to a TIE receptor) of the in vitro translation products of the isolated mRNAs identifies the mRNA and, therefore, the complementary DNA fragments that contain the desired sequences. In addition, specific mRNAs can be selected by adsorption of polysomes isolated from cells to immunobilized antibodies specifically directed against Ang-7 polypeptide. A radiolabeled ANG-7 cDNA can be synthesized using the selected mRNA (from the adsorbed polysomes) as a template. The radiolabeled mRNA or cDNA can then be used as a probe to identify the ANG-7 nucleic acid fragments from among other genomic DNA fragments.

Alternatives to isolating the ANG-7 genomic DNA include, but are not limited to, chemically synthesizing the gene sequence itself from a known sequence or making cDNA to mRNA that encodes an Ang-7 polypeptide. For example, RNA for cDNA cloning of the ANG-7 gene can be isolated from cells that express the Ang-7 polypeptide. Other methods are possible.

The identified and isolated ANG-7 nucleic acids can then be inserted into an appropriate cloning vector. A large number of vector-host systems known in the art can be used. Possible vectors include, but are not limited to, plasmids or modified viruses. The vector system is selected to be compatible with the host cell. Such vectors include, but are not limited to, bacteriophages such as lambda derivatives, yeast integrative and centromeric vectors, 21 plasmid, and derivatives thereof, or plasmids such as pBR322, pUC or pRSETC (InVitrogen, San Diego, Calif.) plasmid derivatives or the Bluescript vector (Stratagene, La Jolla, Calif.), to name a few. The insertion of the ANG-7 nucleic acids into a cloning vector can be accomplished, for example, by ligating the DNA fragment into a cloning vector which has complementary cohesive termini. If the complementary restriction sites used to fragment the DNA are not present in the cloning vector, however, the ends of the DNA molecules can be enzymatically modified. Alternatively, any site desired can be produced by ligating nucleotide sequences (linkers) onto the DNA termini; these ligated linkers can comprise specific chemically synthesized oligonucleotides encoding restriction endonuclease recognition sequences. A restriction site can also be introduced into a nucleic acid by PCR amplification of the nucleic acid using a primer(s) that encodes the desired restriction site(s). In an alternative method, the cleaved vector and ANG-7 nucleic acids can be modified by homopolymeric tailing. Recombinant molecules can be introduced into host cells via transformation, transfection, infection, electroporation, and the like, so that many copies of the gene sequence are generated.

In another method, the ANG-7 gene can be identified and isolated after insertion into a suitable cloning vector in a "shot gun" approach. Enrichment for the ANG-7 gene, for example, by size fractionation, can be done before insertion into the cloning vector. In specific embodiments, transformation of host cells with recombinant DNA molecules that incorporate the isolated ANG-7 gene, cDNA, or synthesized DNA sequence enables generation of multiple copies of the gene. Thus, the gene can be obtained in large quantities by growing transformants, isolating the recombinant DNA molecules from the transformants and, when necessary, retrieving the inserted gene from the isolated recombinant DNA.

In this specific case, the ANG-7 cDNA was isolated by homology with another known angiopoietin, Ang-1. Briefly, fragments of ANG-7 cDNA were isolated by a BLAST search (Altschul et al., *Nucleic Acids Res.* 25:3389–402 (1997)) against the Expressed Sequence Tag ("EST") database (National Center for Biotechnology Information) using the deduced amino acid sequence of Ang-1 as a reference. Two EST's with overlapping sequences were isolated. A full length cDNA fragment encoding the Ang-7 polypeptide was cloned by screening a full-length human cDNA library using a radioactively-labeled EST. Subsequent analysis of the human ANG-7 cDNA (SEQ ID NO:1) identified an open reading frame of 493 amino acids (SEQ ID NO:2). The deduced amino acid sequence encodes a polypeptide of about 57 kDa. Subsequent analysis of the ANG-7 cDNA confirms that it directs the synthesis of a recombinantly expressed polypeptide of that apparent molecular weight, as determined by SDS PAGE. The human Ang-7 polypeptide is 23.9% and 23.5% similar to the Ang-1 and -2 polypeptides, respectively. Amino acid conservation is distributed throughout the length of the two proteins. The expression profile of Ang-7 polypeptide indicates that the polypeptide is expressed in a variety of heavily vascularized tissues, including heart tissues, the uterus, mammary gland and corpus callosum.

A clone harboring the ANG-7 cDNA, ANG-7-cDNA/pGEM, was deposited at the DSMZ-Deutsche Sammlung von Mikroorganismen und Zellkulturen GmbH, Mascheroder Weg 1b, D-38124 Braunschweig, Germany, on Jun. 26, 2000, under Deposit Registration No. DSM 13562. This deposit was made under the provisions of the Budapest Treaty on the International Recognition of the Deposit of Microorganisms for the Purpose of Patent Procedure and the Regulation thereunder (Budapest Treaty).*Ang-7 Polypeptides, Fragments, Variants, Derivatives and Analogs:*

The invention further relates to Ang-7 polypeptides, and biologically active or diagnostically or therapeutically useful fragments, variants, derivatives and analogs thereof, and their use in modulating angiogenesis. In one embodiment, the Ang-7 polypeptide has the amino acid sequence of SEQ ID NO:2. In another embodiment, the Ang-7 polypeptide is a fragment, variant, derivative or analog of SEQ ID NO:2. The Ang-7 polypeptide, fragment, variant, derivative or analog is biologically active. A biologically active Ang-7 polypeptide, fragment, variant, derivative or analog refers to the molecule's ability to modulate angiogenesis such as, for example, by affecting endothelial tube formation, as described in, for example, the HUVEC assay in Example 9 (infra), or by affecting tumor cell growth or proliferation (e.g., see Example 10). Alternatively, such polypeptides, fragments, variants, derivatives or analogs which have the desired immunogenicity or antigenicity can be used in immunoassays, for immunization, for inhibition of Ang-7 polypeptide activity, and the like. Similarly, Ang-7 fragments, variants, derivatives or analogs that retain, or alternatively lack or inhibit, a desired Ang-7 property of interest (e.g., inhibition of angiogenesis) can be used as inducers, or inhibitors of such property and its physiological correlates. A specific embodiment relates to an Ang-7 fragment that can be administered to a subject to inhibit angiogenesis. Fragments, variants, derivatives or analogs of Ang-7 can be tested for the desired activity by procedures known in the art, including but not limited to the assays described herein.

In another embodiment, an Ang-7 polypeptide, fragment, variant, derivative or analog has at least 10 contiguous amino acids. In other embodiments, the Ang-7 polypeptide, fragment, variant, derivative or analog consists of at least 20 or 50 contiguous amino acids. In another embodiment, the Ang-7 polypeptide, fragments, variants, derivatives or analogs are not larger than 35, 100 or even 200 amino acids. Fragments, variants, derivatives and analogs of Ang-7 polypeptide include but are not limited to those molecules comprising regions that are substantially similar to an Ang-7 polypeptide (e.g., in various embodiments, at least 60%, or 70%, or 80%, or 90%, or up to 95% identity over an amino acid sequence of identical size), or when compared to an aligned sequence in which the alignment is done by a computer sequence comparison/alignment program known in the art, or when the encoding nucleic acid is capable of hybridizing to an ANG-7 nucleic acid, under stringent, moderately stringent, or low stringency conditions.

Ang-7 polypeptide variants, derivatives or analogs can be made by altering Ang-7 sequences by substitutions, additions or deletions that provide for functionally equivalent molecules. Ang-7 polypeptide variants, derivatives or analogs include, but are not limited to, those containing as a primary amino acid sequence of all or part of the amino acid sequence of an Ang-7 polypeptide including altered sequences in which functionally equivalent amino acid residues (i.e., conservative substitutions) are substituted for residues within the sequence, resulting in a silent change. For example, one or more amino acid residues within the sequence can be substituted by another amino acid of a similar polarity, hydrophobicity or hydrophilicity, which acts as a functional equivalent, thereby resulting in a silent alteration. Substitutes for an amino acid within the sequence can be selected from other members of the class to which the amino acid belongs.

Ang-7 polypeptide variants, fragments, derivatives and analogs can be produced by various methods known in the art. The manipulations which result in their production can occur at the gene or protein level. For example, the cloned ANG-7 gene or cDNA sequence can be modified by any of numerous strategies known in the art (see, e.g., Sambrook et al., *Molecular Cloning, A Laboratory Manual*, 2d Ed., Cold Spring Harbor Laboratory Press, Cold Spring Harbor, N.Y. (1989)). The sequence can be cleaved at appropriate sites with restriction endonuclease(s), followed by further enzymatic modification if desired, isolated, and ligated in vitro. In the production of a nucleic acid encoding an Ang-7 polypeptide, or fragment, variant, derivative or analog thereof, the modified nucleic acid remains in the proper translational reading frame, so that the reading frame is not interrupted by translational stop signals or other signals which interfere with the synthesis. An ANG-7 nucleic acid can also be mutated in vitro or in vivo to create and/or destroy translation, initiation and/or termination sequences. The nucleic acid sequence encoding an Ang-7 polypeptide can also be mutated to create variations in coding regions and/or to form new restriction endonuclease sites or destroy preexisting ones and to facilitate further in vitro modification. Any technique for mutagenesis known in the art can be used, including but not limited to chemical mutagenesis, in vitro site-directed mutagenesis (Hutchinson et al., *J. Biol. Chem.* 253:6551 (1978)), the use of TAB® linkers (Pharmacia), and the like.

Manipulations of the Ang-7 polypeptide sequence can also be made at the protein level. Included within the scope of the invention are Ang-7 polypeptide variants, derivatives or analogs which are chemically modified during or after translation (e.g., by glycosylation, acetylation, phosphorylation, amidation, derivatization by known protecting/blocking groups, proteolytic cleavage, linkage to an antibody molecule or other cellular ligand, and the like). Any of numerous chemical modifications can be carried out by known techniques, including, but not limited to, specific chemical cleavage (e.g., by cyanogen bromide); enzymatic cleavage (e.g., by trypsin, chymotrypsin, papain, V8 protease, and the like); modification by, for example, $NaBH_4$, acetylation, formylation, oxidation and reduction, or metabolic synthesis in the presence of tunicamycin, and the like.

In addition, Ang-7 polypeptides, or fragments, variants, derivatives and analogs thereof can be chemically synthesized. For example, a peptide corresponding to a portion, or fragment, of an Ang-7 polypeptide, which comprises a desired domain, or which mediates a desired activity in vitro, can be synthesized by use of chemical synthetic methods using for example an automated peptide synthesizer. Ang-7 polypeptide analogs can be prepared, if desired, by introducing non-classical amino acids or chemical amino acid analogs as a substitution or addition into the Ang-7 polypeptide sequence. Non-classical amino acids include, but are not limited to, the D-isomers of the common amino acids, α-amino isobutyric acid, 4-aminobutyric acid, 2-amino butyric acid, γ-amino butyric acid, ∈-Ahx, 6-amino hexanoic acid, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, selenocysteine, fluoro-amino acids, designer amino acids such as β-methyl amino acids, C α-methyl amino acids, N α-methyl amino acids, and amino acid analogs in general. Furthermore, the amino acid can be D (dextrorotary) or L (levorotary).

In an embodiment, the Ang-7 polypeptide, or fragment, derivative or analog thereof is a chimeric, or fusion protein, comprising an Ang-7 polypeptide or variant, fragment, derivative or analog thereof (typically consisting of at least a domain or motif of the Ang-7 polypeptide, or at least 10 contiguous amino acids of the Ang-7 polypeptide) joined at its amino- or carboxy-terminus via a peptide bond to an amino acid sequence of a different protein. In one embodiment, such a chimeric protein is produced by recombinant expression of a nucleic acid encoding the protein. The chimeric product can be made by ligating the appropriate nucleic acid sequence, encoding the desired amino acid sequences to each other by methods known in the art, in the proper coding frame and expressing the chimeric product by methods commonly known in the art. Alternatively, the chimeric product can be made by protein synthetic techniques (e.g., by use of an automated peptide synthesizer).

Expression of ANG-7 Nucleic Acids or Ang-7 Polypeptides

In a further embodiment, host cells comprise a construct expressing an ANG-7 nucleic acid. Such a host cell can be a higher eukaryotic cell, such as a mammalian cell, a lower eukaryotic cell, such as a yeast cell, or a prokaryotic cell, such as a bacterial cell. Introduction of the construct into the host cell can be effected by calcium phosphate transfection, DEAE-dextran mediated transfection, or electroporation (Davis et al. *Basic Methods in Molecular Biology*, 2nd ed., Appleton and Lang, Paramount Publishing, East Norwalk, Conn. (1994)), calcium chloride-mediated transformation, lithium acetate-mediated transformation, and the like.

The constructs in host cells can be used in a conventional manner to produce the Ang-7 polypeptide, or fragment, variant, derivative or analog thereof. Cell-free translation systems can also be employed to produce such polypeptides using RNA's derived from the ANG-7 nucleic acid. Alternatively, the Ang-7 polypeptide, fragment, variant, derivative or analog thereof can be synthetically produced by conventional peptide synthesizers.

ANG-7 nucleic acids can be expressed in mammalian cells, yeast, bacteria, insect or other cells under the control of appropriate promoters. Representative expression vectors include plasmid, phage and/or viral vector sequences, such as those described by Sambrook et al., *Molecular Cloning: A Laboratory Manual* (Second Edition, Cold Spring Harbor, N.Y., (1989)). For example, suitable vectors include adenoviral vectors, retroviral vectors, including lentiviral vectors, vaccinia viral vectors, *cytomegalovirus* viral vectors, and baculovirus vectors (see, e.g. Knops et a, *J. Biol. Chem.* 266:7285 (1991)), and the like. DNA sequences derived from the SV40 viral genome, for example, SV40 origin, early promoter, enhancer, splice, and polyadenylation sites, can be used to provide the required nontranscribed genetic elements. Representative, useful vectors include pRc/CMV and pcDNA3 vectors (Invitrogen, San Diego, Calif.).

Promoters capable of directing the transcription of a nucleic acid can be inducible or constitutive promoters and include viral and cellular promoters. For expression in mammalian host cells, suitable viral promoters include the immediate early *cytomegalovirus* promoter (Boshart et al., *Cell* 41:521–30 (1985)) and the SV40 promoter (Subramani et al., *Mol. Cell. Biol.* 1:854–64 (1981)). Suitable cellular promoters for expression of nucleic acids in mammalian host cells include, but are not limited to the mouse metallothionien-1 promoter (Palmiter et al., U.S. Pat. No. 4,579,821), and tetracycline-responsive promoter (Gossen and Bujard, *Proc. Natl. Acad. Sci. USA* 89:5547–51 (1992); Pescini et al., *Biochem. Biophys. Res. Comm.* 202:1664–67 (1994)). Transcription termination signals are also typically located downstream of the coding sequence of interest. Suitable transcription termination signals include the early or late polyadenylation signals from SV40 (Kaufman and Sharp, *Mol. Cell. Biol.* 2:1304–19 (1982)), the polyadenylation signal from the Adenovirus 5 e1B region, and the human growth hormone gene terminator (DeNoto et al., *Nucleic Acid. Res.* 9:3719–30 (1981)).

Transcription of ANG-7 nucleic acids in mammalian cells is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a *cytomegalovirus* early promoter enhancer, a polyoma enhancer on the late side of the replication origin, and adenovirus enhancers.

Mammalian cells can be transfected by a number of methods including calcium phosphate precipitation (see, e.g., Wigler et al., *Cell* 14:725 (1978); Corsaro and Pearson, *Somatic Cell Genetics* 7:603 (1981); Graham and Van der Eb, *Virology* 52:456 (1973)); lipofection (see, e.g., Felgner et al., *Proc. Natl. Acad. Sci. USA* 84: 7413–17 (1987)) and microinjection and electroporation (see, e.g., Neumann et al., *EMBO J.* 1: 841–45 (1982)). Mammalian cells can be transduced with virus such as SV40, CMV and the like. In the case of viral vectors, cloned DNA molecules can be introduced by infection of susceptible cells with viral particles. Retroviral, including lentiviral, and adenoviral vectors are preferred for use in expressing ANG-7 nucleic acids in mammalian cells, particularly when ANG-7 nucleic acids or fragments, variants, derivatives or analogs thereof are used in methods of gene therapy.

Selectable markers are typically used to identify cells that contain the ANG-7 nucleic acids. Selectable markers are generally introduced into the cells along with the cloned DNA molecules and include genes that confer resistance to drugs, such as neomycin, hygromycin and methotrexate. Selectable markers can also complement auxotrophies in the host cell. Yet other selectable markers provide detectable signals, such as β-galactosidase or green fluorescent protein, to identify cells containing ANG-7 nucleic acids. Selectable markers can be amplifiable. Such amplifiable selectable markers can be used to amplify the number of sequences integrated into the host genome.

Various mammalian cell culture systems can be employed to express ANG-7 nucleic acids. Examples of mammalian expression systems include the COS-7 lines of monkey kidney fibroblasts (see, e.g., Gluzman, *Cell* 23:175 (1981)), and other cell lines capable of expressing a compatible vector, such as the C127, 3T3, CHO, HeLa, BHK, VERO, HeLa, MDCK, 293, W138, HEK, HUVEC cell lines. Once established, such cell lines can be grown in culture. Methods for culturing human cells in vitro and for immortalizing cells are known to the skilled artisan.

For long-term, high-yield production of recombinant polypeptides, stable expression is preferred. For example, cell lines which stably express constructs containing the ANG-7 nucleic acids can be engineered. Rather than using expression vectors that contain viral origins of replication, host cells can be transformed with ANG-7 nucleic acids, by appropriate expression control elements (e.g., promoter and enhancer sequences, transcription terminators, polyadenylation sites, and the like), and a selectable marker. Following the introduction of such an expression vector into mammalian cells, engineered cells can be allowed to grow for 1–2 days in an enriched media, and then switched to a selective media. The selectable marker in the expression vector confers resistance to the selection and allows cells to stably integrate the vector into the chromosome and grow to form foci which in turn can be cloned and expanded into cell lines.

A number of selection systems can be used, including, but not limited, to the herpes simplex virus thymidine kinase ("tk") (see, e.g., Wigler et al., *Cell* 11:223 (1977)), hypoxanthine-guanine phosphoribosyltransferase ("hprt") (sec, e.g., Szybalski et al., *Proc. Natl. Acad. Sci. USA* 48:2026 (1962)), and adenine phosphoribosyl-transferase genes ("aprt") (see, e.g., Lowy et al., *Cell* 22: 817 (1980)) and can be employed in tk⁻, hgprt⁻ or aprt⁻ cells, respectively. Antimetabolite resistance can also be used as the basis of selection for dihydrofolate reductase ("dhfr"), which confers resistance to methotrexate (Wigler et al., *Proc. Natl. Acad. Sci. USA* 77:3567(1980); O'Hare et al., *FEBS Lett.* 210:731 (1981)); gpt, which confers resistance to mycophenolic acid (Mulligan et al., *Proc. Natl. Acad. Sci. USA* 78:2072. (1981)); neomcyin, which confers resistance to the aminoglycoside G-418 (Colberre-Garapin et al., *J. Mol. Biol.* 150:1 (1981)); and hygromycin, which confers resistance to hygromycin (Santerre et al., *Gene* 30:147 (1984)).

ANG-7 nucleic acids can also be expressed in *Saccharomyces cerevisiae, Schizosaccharomyces prombe*, filamentous fungi, and other single and multicellular organisms that are amenable to transformation and/or transfection. Methods for expressing cloned genes in *Saccharomyces cerevisiae* are generally known in the art. (See, e.g., "Gene Expression Technology" In *Methods in Enzymology*, Vol. 185, Goeddel (ed.), Academic Press, San Diego, Calif. (1990); "Guide to Yeast Genetics and Molecular Biology" In *Methods in Enzymology*, Guthrie and Fink (eds.), Academic Press, San Diego, Calif. (1991)). Filamentous fungi (e.g., strains of *Aspergillus*) can also be used to express the ANG-7 nucleic acids. Methods for expressing heterologous genes and cDNAs in cultured mammalian cells and in *E. coli* are discussed in detail in Sambrook et al. (*Molecular Cloning: A Laboratory Manual*, Second Edition, Cold Spring Harbor, N.Y. (1989)). As would be evident to one skilled in the art, one can express ANG-7 nucleic acids in other host cells such as avian, insect and plant cells using regulatory sequences, vectors and methods well established in the literature.

Recombinant expression vectors useful for expression in bacterial typically include origins of replication and selectable markers permitting transformation of the host cell (e.g., the ampicillin or tetracycline resistance genes of *E. coli* or the TRP1 or URA3 gene of *S. cerevisiae*), and a promoter derived from a highly-expressed gene to direct transcription of a downstream structural sequence. Such promoters can be derived from operons encoding glycolytic enzymes, such as 3-phosphoglycerate kinase (PGK), alpha factor, acid phosphatase, heat shock proteins, translation elongation factor, and the like. The heterologous ANG-7 nucleic acid is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics (e.g., stabilization or simplified purification of expressed recombinant product). Suitable prokaryotic hosts for transformation include *Escherichia coli, Bacillus subtilis, Salmonella typhimurium* and various species within the genera *Pseudomonas, Streptomyces*, and *Staphylococcus*, although others can also be employed as a routine matter of choice.

Useful expression vectors for bacterial use comprise a selectable marker and bacterial origin of replication derived from plasmids comprising genetic elements of the well-known cloning vector pBR322 (ATCC 37017). Other vectors include but are not limited to, pBLUESCRIPT vectors (Stratagene), PKK223-3 (Pharmacia Fine Chemicals, Uppsala, Sweden) and GEM1 (Promega Biotec, Madison, Wis.). These pBR322 "backbone" sections are combined with an appropriate promoter and the structural sequence to be expressed.

Useful expression vectors further comprise a fusion partner for ease in purifying a desired polypeptide or for producing soluble polypeptides. Examples of commercial fusion vectors include but are not limited to pET32a (Novagen, Madison, Wis.), pGEX-4T-2 (Pharmacia) and pCYB3 (New England Biolabs, Beverly, Mass.). Expression vectors which avoid the use of fusion partners can also be constructed particularly for high level expression of Ang-7 polypeptides, or fragments, variants, derivatives or analogs thereof in bacterial cells. For example, vectors can be made to optimize translational coupling, as described by Pilot-Matias et al. (*Gene* 128:219–225 (1993)). Alternatively, an ANG-7 nucleic acid can be co-expressed with a separate accessory plasmid which itself encodes a protein or peptide that aids in solubilizing an Ang-7 polypeptide of interest. (See, e.g., Makrides, *Microbiological Reviews* 60:512 (1996)).

Following transformation of a suitable host strain and growth of the host strain to an appropriate cell density, the selected promoter is derepressed by appropriate means (e.g., temperature shift or chemical induction), and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents; such methods are well-known to the ordinary artisan.

Ang-7 polypeptides can be isolated using a number of established methods, such as affinity chromatography using anti-Ang-7 antibodies coupled to a solid support and sequence-specific chromatography as described by Lobanenkov et al. (*Oncogene* 5:1743–53 (1990)) and using antibodies against an epitope-tagged Ang-7 polypeptide (e.g., anti-$HIS_4$, myc, FLAG, and the like). Additional isolation methods include purification means such as liquid chromatography, high pressure liquid chromatography, FPLC, gradient centrifugation and gel electrophoresis, among others. Methods of protein purification are known in the art and can be applied to the purification of recombinant polypeptides described herein. (See generally, Scopes, *Protein Purification*, Springer-Verlag, NY (1982)).

Anti-Ang-7 Antibodies

In another embodiment, the invention provides anti-Ang-7 antibodies for use in modulating angiogenesis. Such antibodies can bind to Ang-7 polypeptides, or fragments, variants, derivatives or analogs thereof. Ang-7 polypeptides can be used to raise antisera or monoclonal antibodies following, for example, the method of Kohler and Milstein (*Nature* 256:495 (1975)). Such monoclonal antibodies can then form the basis for a treatment, therapeutic use, or diagnostic test.

The production of non-human antisera or monoclonal antibodies (L&, murine, lagormorpha, porcine or equine) can be accomplished by, for example, immunizing an animal with Ang-7 polypeptides, fragments, variants, derivatives or analogs, with or without an adjuvant. For the production of monoclonal antibodies, antibody producing cells are obtained from immunized animals, immortalized and screened, or screened first for the production of the antibody that binds to the antigen, and then immortalized. It can be desirable to transfer the antigen binding regions (e.g., F(ab'), F(ab')$_2$, Fv, or hypervariable regions) of non-human antibodies into the framework of a human antibody by recombinant DNA techniques to produce a substantially human molecule. Methods for producing such "humanized" molecules are generally well known and described in, for example, U.S. Pat. Nos. 4,816,567; 4,816,397; 5,693,762; and 5,712,120; International Patent Publication WO 87/02671 and WO 90/00616; and European Patent Publication 0,239,400; the disclosures of which are incorporated by reference herein). Alternatively, a human monoclonal antibody or portions thereof can be identified by first screening a human B-cell cDNA library for DNA molecules that encode antibodies that specifically bind to an Ang-7 polypeptide according to the method generally set forth by Huse et al. (*Science* 246:1275–81 (1989)). The DNA molecule can then be cloned and amplified to obtain sequences that encode the antibody (or binding domain) of the desired specificity. Phage display technology offers another technique for selecting antibodies that bind to Ang-7 polypeptides. (See, e.g., International Patent Publications WO 91/17271 and WO 92/01047, and Huse et al., supra).

Antibodies can also be produced by genetic immunization using expression vectors to direct the expression of Ang-7 polypeptides. Particle bombardment-mediated gene transfer (Tang et al., *Nature* 356:152–54 (1992); Eisenbaum et al., *DNA & Cell Biol.* 12:791–97 (1993); Johnston and Tang, *Meth. Cell Biol.* 43 Pt.A:353–65 (1994); Vahlsing et al., *J. Immun. Meth.* 175:11–22 (1994)) and retroviral gene transfer (Wang et a, *DNA & Cell Biol.* 12:799–805 (1993); Stover, *Curr. Opin. Immunol.* 6:568–71 (1994); Laube et al., *Human Gene Ther.* 5:853–62 (1994)) have been used to generate specific antibody responses to proteins encoded by transferred genes. These methods permit the production of antibodies without requiring protein purification. Such methods can be used to produce panels of antibodies specific to Ang-7 polypeptides. Monoclonal antibodies can also be generated using these methods.

Antibodies against Ang-7 polypeptides can be used as reagents to detect Ang-7 polypeptides in biological samples, such as tumor biopsy samples, tissue and organ sections, peripheral blood cells, and the like. Such antibodies can also be used in immunoassays to detect and/or quantitate Ang-7 polypeptide levels. Immunoassays suitable for use in the present invention include, but are not limited to, enzyme-linked immunosorbant assays, immunoblots, inhibition or competition reactions, sandwich assays, radioimmunoprecipitation, and the like. (See, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, NY (1988)).

In one assay, Ang-7 polypeptides are identified and/or quantified using labeled antibodies, preferably labeled monoclonal antibodies. The antibodies are reacted with tissues or cells, and then the tissues or cells are examined to determine whether the antibodies specifically bound to the target Ang-7 polypeptide. Such assays are typically performed under conditions conducive to immune complex formation. Unlabeled primary antibody can be used in combination with labels that are reactive with primary antibody to detect the Ang-7 polypeptide. For example, the primary antibody can be detected indirectly by a labeled secondary antibody made to specifically detect the primary antibody. Alternatively, the anti-Ang-7 antibody can be directly labeled. A wide variety of labels can be employed, such as radionuclides, particles (I, gold, ferritin, magnetic particles and red blood cells), fluorophores, chemiluminescers, enzymes, enzyme substrates, enzyme cofactors, enzyme inhibitors, ligands (particularly haptens), and the like.

The anti-Ang-7 polypeptides can be used in a diagnostic assay for detecting levels of polypeptides of the present invention, for example, in various tissues, since an underexpression of the proteins compared to normal control tissue samples may detect the presence of abnormal angiogenesis, for example, a tumor. Assays used to detect levels of protein in a sample derived from a host are well-known to those of skill in the art and include radioimmunoassays, competitive-binding assays, Western blot analyses, ELISA assays and "sandwich" type assays. Diagnostic assays also include the detection of polynucleotides which code for the polypeptides of the present invention.

Methods of Using ANG-7 Nucleic Acids and/or Ang-7 Polypeptides:

In another embodiment, methods and compositions are provided for the administration of an Ang-7 compound to modulate angiogenesis. Ang-7 compounds include, but are not limited to, Ang-7 polypeptides, fragments, variants, derivatives and analogs thereof, as described herein. Such Ang-7 compounds can further include ANG-7 nucleic acids encoding Ang-7 polypeptide, fragments or variants, as described herein, and ANG-7 antisense nucleic acids, as more fully described below. Disorders involving angiogenesis, such as unwanted angiogenesis, use an Ang-7 compound that inhibits angiogenesis, such as the administration of Ang-7 polypeptides, fragments, variants, derivatives and/or analogs thereof and/or ANG-7 nucleic acids. Similarly, disorders in which angiogenesis is deficient or is desired can be treated by administration an ANG-7 antisense nucleic acid, or an Ang-7 polypeptide, a fragment, variant, derivative or analog thereof that inhibits Ang-7 function. In another embodiment, Ang-7 compounds include antibodies, such as polyclonal, monoclonal and humanized antibodies.

The compounds can be administered therapeutically or prophylactically. They can be contacted with the host cell in vivo, ex vivo, or in vitro, in an effective amount, as demonstrated by the following examples.

Gene Therapy

ANG-7 nucleic acids coding for Ang-7 polypeptides of the present invention, can be used in a process of gene therapy. Gene therapy refers to the process of providing for the expression of nucleic acid sequences of exogenous origin in a subject for the treatment of a disease or clinical condition within that subject. Such gene therapy can be involved in the treatment of a disease or clinical condition which can include, but is not limited to, cancer, wound healing, diabetic retinopathies, macular degeneration, cardiovascular diseases, and clinical conditions involving angiogenesis in the reproductive system, including regulation of placental vascularization or use as an abortifacient. Delivery of the nucleic acid into a subject can be either direct, in which case the patient is directly exposed to the nucleic acid or nucleic acid-carrying vector, or indirect, in which case cells are first transformed with the nucleic acid in vitro, then transplanted into the patient. These two approaches are known, respectively, as in vivo, or ex vivo gene therapy. For example, Ang-7 polypeptide, or a fragment or variant thereof, can be recombinantly expressed by engineering cells with a polynucleotide (DNA or RNA) coding for the polypeptide, fragment or variant ex vivo, the engineered cells are then provided to a patient to be treated with the polypeptide. Cells can also be engineered by procedures known in the art by use of a retroviral/lentiviral particle containing RNA encoding the Ang-7 polypeptide, fragment of variant. Exemplary methods are described below.

For general reviews of the methods of gene therapy, see Goldspiel et al. (*Clinical Pharmacy* 12:488–505 (1993)); Wu and Wu (*Biotherapy* 3:87–95 (1991)); Tolstoshev (*Ann. Rev. Pharmacol. Toxicol.* 32:573–596 (1993)); Mulligan (Science 260:926–932 (1993)); Morgan and Anderson (*Ann. Rev. Biochem.* 62:191–217 (1993)); and May (*TIBTECH* 11:155–215 (1993)). Methods commonly known in the art of recombinant DNA technology that can be used include those described in Ausubel et al. (*Current Protocols in Molecular Biology*, John Wiley & Sons, NY (1993)); Kriegler (*Gene Transfer and Expression, A Laboratory Manual*, Stockton Press, NY (1990)); and U.S. Pat. Nos. 6,077,663; 6,077,835; 6,077,705; and 6,075,012. Methods using other exogenous sequences for gene therapy are also applicable to gene therapy using ANG-7 nucleic acids. (See A, U.S. Pat. No. 6,066,624).

Several methods for transferring potentially therapeutic genes to defined cell populations are known. (e, e.g. Mulligan, *Science* 260:926–31 ((1993).) These methods include:

1) Direct gene transfer. (See, e.g., Wolff et al., *Science* 247:1465–68 (1990)).
2) Liposome-mediated DNA transfer. (See, e.g., Caplen et al., *Nature Med,* 3:39–46 (1995); Crystal, *Nature Med.* 1:15–17 (1995); Gao and Huang, *Biochem. Biophys. Res. Comm.* 179:280–85 (1991)).
3) Retrovirus-mediated DNA transfer. (See, e.g., Kay et al., *Science,* 262:117–19 (1993); Anderson, *Science* 256:808–13 (1992)). Retroviruses from which the retroviral plasmid vectors hereinabove mentioned can be derived include lentiviruses. They further include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, Myeloproliferative Sarcoma Virus, and mammary tumor virus. In one embodiment, the retroviral plasmid vector is derived from Moloney Murine Leukemia Virus. Examples illustrating the use of retroviral vectors in gene therapy further include the following: Clowes et al. (*J. Clin. Invest.* 93:644–651 (1994)); Kiem et al. (*Blood* 83:1467–1473 (1994)); Salmons and Gunzberg (*Human Gene Therapy* 4:129–141 (1993)); and Grossman and Wilson (*Curr. Opin. in Genetics and Devel.* 3:110–114 (1993)).
4) DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). (See, e.g. Ali et al., *Gene Therapy* 1:367–84 (1994); U.S. Pat. Nos. 4,797,368 and 5,139,941, the disclosures of which are incorporated herein by reference.) Adenoviruses have the advantage that they have a broad host range, can infect quiescent or terminally differentiated cells, such as neurons or hepatocytes, and appear essentially non-oncogenic. Adenoviruses do not appear to integrate into the host genome. Because they exist extrachromosomally, the risk of insertional mutagenesis is greatly reduced. Adeno-associated viruses exhibit similar advantages as adenoviral-based vectors. However, AAVs exhibit site-specific integration on human chromosome 19.

Kozarsky and Wilson (*Current Opinion in Genetics and Development* 3:499–503 (1993)) present a review of adenovirus-based gene therapy. Bout et al. (*Human Gene Therapy* 5:3–10 (1994)) demonstrated the use of adenovirus vectors to transfer genes to the respiratory epithelia of rhesus monkeys. Herman et al. (*Human Gene Therapy* 10:1239–1249 (1999)) describe the intraprostatic injection of a replication-deficient adenovirus containing the herpes simplex thymidine kinase gene into human prostate, followed by intravenous administration of the prodrug ganciclovir in a phase I clinical trial. Other instances of the use of adenoviruses in gene therapy can be found in Rosenfeld et al. (*Science* 252:431–434 (1991)); Rosenfeld et al. (*Cell* 68:143–155 (1992)); Mastrangeli et al. (*J. Clin. Invest.* 91:225–234 (1993)); and Thompson (*Oncol. Res.* 11:1–8 (1999)).

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity. However, recent developments in the field of lentiviral vectors may circumvent some of these limitations. (See Naldini et al., *Science* 272:263–7 (1996).)

Gene therapy with DNA encoding a polypeptide of the present invention is provided to a subject (e.g., a patient or mammal) in need thereof, concurrent with, or immediately after diagnosis. The skilled artisan will appreciate that any suitable gene therapy vector containing DNA encoding a polypeptide of the present invention can be used in accordance with the present invention. The techniques for constructing such a vector are known. (See, e.g., Anderson, *Nature* 392 25–30 (1998); Verma, *Nature* 389 239–42 (1998)). Introduction of the vector to the target site can be accomplished using known techniques.

In one embodiment, ANG-7 nucleic acid is inserted into an expression vector. The ANG-7 nucleic acids encode an Ang-7 polypeptide, fragment, variant, derivative or chimeric protein. In particular, such an expression vector construct typically comprises a promoter operably linked to an ANG-7 nucleic acid (e.g. cDNA or a portion of the coding region), the promoter being inducible or constitutive, and, optionally, tissue-specific.

In another embodiment, if an endogenous ANG-7 nucleic acid is defective, the defective sequences can be replaced by exogenous ANG-7 coding sequences and any other desired sequences that are flanked by regions that promote homologous recombination at a desired site in the genome, thus providing for intrachromosomal expression of the exogenous ANG-7 nucleic acid. (See e.g., Koller and Smithies, *Proc. Natl. Acad. Sci. USA* 86:8932–8935 (1989); Zijlstra et al., *Nature* 342:435–438 (1989)); U.S. Pat. Nos. 5,631,153; 5,627,059; 5,487,992; and 5,464,764.).

Nucleic acids can also administering in linkage to a peptide which is known to enter the nucleus, by administering the nucleic acid in linkage to a ligand subject to receptor-mediated endocytosis (see e.g., Wu and Wu,*J. Biol. Chem.* 262:4429–4432 (1987)), which can be used to target cell types specifically expressing the receptors, and the like. In another embodiment, a nucleic acid-ligand complex can be formed in which the ligand comprises a fusogenic viral peptide to disrupt endosomes, allowing the nucleic acid to avoid lysosomal degradation.

In yet another embodiment, the nucleic acid can be targeted in vivo for cell specific uptake and expression, by targeting a specific receptor (e.g., International Patent Publications WO 92/06180; WO 92/22635; WO 92/20316; WO 93/14188, and WO 93/20221). Alternatively, the nucleic acid can be introduced intracellularly and incorporated within host cell DNA for expression by homologous recombination. (See, e.g., Koller and Smithies, *Proc. Natl. Acad. Sci. USA* 86:8932–8935 (1989); Zijlstra et al., *Nature* 342:435438 (1989); U.S. Pat. Nos. 5,631,153; 5,627,059; 5,487,992; and 5,464,764).)

In a specific embodiment, a viral vector is used that contains an ANG-7 nucleic acid. For example, a retroviral vector can be used (see Miller et al., *Meth. Enzymol.* 17:581–599 (1993)). These retroviral vectors have been modified to delete retroviral sequences that are not necessary for packaging of the viral genome and integration into host cell DNA. The ANG-7 nucleic acid to be used in gene therapy is cloned into the vector, which facilitates delivery of the gene into a patient. More detail about retroviral vectors can be found in Boesen et al. (*Biotherapy* 6:291–302 (1994)), which describes the use of a retroviral vector to deliver the molrl gene to hematopoietic stem cells in order to make the stem cells more resistant to chemotherapy.

Other approaches to gene therapy involve transferring a gene to cells in tissue culture by methods such as electroporation, lipofection, calcium phosphate mediated transfection, or viral infection. Typically, the method includes the transfer of a selectable marker to the cells. The cells are then placed under selection to isolate those cells that have taken up and are expressing the transferred gene. The selected cells are then delivered to a patient.

Numerous techniques are known in the art for the introduction of foreign genes into cells (see, e.g., Loeffler and Behr, *Meth. Enzymol.* 217:599–618 (1993); Cohen et al., *Meth. Enzymol.* 217:618–644 (1993); Cline, *Pharmac. Ther.* 29:69–92 (1985)) and can be used in accordance with the present invention. The technique typically provides for the stable transfer of the nucleic acid to the cell, so that the nucleic acid is expressible by the cell and is heritable and expressible by its cell progeny.

The resulting recombinant cells can be delivered to a patient by various methods known in the art. Typically, cells are injected subcutaneously. Alternatively, recombinant skin cells can be applied as a skin graft onto the patient. Recombinant blood cells (e.g., hematopoietic stem or progenitor cells) are typically administered intravenously. The amount of cells envisioned for use depends on the desired effect, the patient's condition, and the like, and can be determined by one skilled in the art.

Cells into which a nucleic acid can be introduced for purposes of gene therapy encompass any desired, available cell type, and include but are not limited to endothelial cells, prostate cells, epithelial cells, keratinocytes, fibroblasts, muscle cells, hepatocytes, blood cells (such as T lymphocytes, B lymphocytes, monocytes, macrophages, neutrophils, eosinophils, megakaryocytes and granulocytes), various stem or progenitor cells (in particular, hematopoietic stem or progenitor cells, such as those obtained from bone marrow, umbilical cord blood, peripheral blood, fetal liver, and the like). The cells used for gene therapy generally are autologous to the patient, but heterologous cells that can be typed for compatibility with the patient can be used.

Administration of Ang-7 Polypeptides, or Fragments, Variants, Derivatives or Analogs Thereof:

The invention provides methods for the administration to a subject of an effective amount of an Ang-7 compound. For example, unwanted angiogenesis can be treated or prevented by administration of an effective amount of Ang-7 polypeptide, fragment, variant, derivative or analog thereof. In one embodiment, such polypeptides are administered therapeutically (including prophylactically) in diseases or clinical condition involving increased (relative to normal or desired) angiogenesis, to thereby inhibit angiogenesis. In another embodiment, such polypeptides are administered therapeutically (including prophylactically) in diseases or clinical conditions where angiogenesis may be relevant to the causation or treatment of the disease or clinical condition in order to inhibit the disease or clinical condition. The diseases or clinical conditions of the present invention include but are not limited to, cancer, wound healing, tumor formation, diabetic retinopathies, macular degeneration, cardiovascular diseases, and the like.

Typically, the Ang-7 compound is substantially purified prior to formulation. The subject can be an animal, including but not limited to, cows, pigs, horses, chickens, cats, dogs, and the like, and is typically a mammal, and in a particular embodiment human. In another specific embodiment, a non-human mammal is the subject. Formulations and methods of administration that can be employed when the Ang-7 compound comprises a nucleic acid are described above; additional appropriate formulations and routes of administration can be selected from among those described below.

Various delivery systems are known and can be used to administer an Ang-7 compound, such as, for example, encapsulation in liposomes, microparticles, microcapsules, recombinant cells capable of expressing the compound, receptor-mediated endocytosis (see, e.g., Wu and Wu, *J. Biol. Chem.* 262:4429–4432 (1987)), construction of an expression vector comprising an ANG-7 nucleic acid as part of a retroviral or other vector, and the like. Methods of introduction include but are not limited to, intradermal, intramuscular, intraperitoneal, intravenous, subcutaneous, intranasal, epidural and oral routes. The compounds can be administered by any convenient route, for example, by infusion or bolus injection, by absorption through epithelial or mucocutaneous linings (e.g., oral mucosa, rectal and intestinal mucosa) and the like, and can be administered together with other biologically active agents. Administration can be systemic or local.

In a specific embodiment, it can be desirable to administer an Ang-7 compound locally to the area in need of treatment; this administration can be achieved by, for example, and not by way of limitation, local infusion during surgery, topical application (e.g., in conjunction with a wound dressing after surgery), by injection, by means of a catheter, by means of a suppository, or by means of an implant, the implant being of a porous, non-porous, or gelatinous material, including membranes such as sialastic membranes, or fibers. In one embodiment, administration can be by direct injection at the site (or former site) of a malignant tumor or neoplastic or pre-neoplastic tissue.

In another embodiment, the Ang-7 compound can be delivered in a vesicle, in particular a liposome (see Langer, *Science* 249:1527–1533 (1990); Treat et al., In *Liposomes in the Therapy of Infectious Disease and Cancer*, Lopez-Berestein and Fidler (eds.), Liss, New York, pp. 353–365 (1989); Lopez-Berestein, supra, pp. 317–327); U.S. Pat. Nos. 6,077,663 and 6,071,533).

In yet another embodiment, the Ang-7 compound can be delivered in a controlled release system. In one embodiment, a pump can be used (see Langer, supra; Sefton, *CRC Crit. Ref. Biomed. Eng.* 14:201 (1987); Buchwald et al, *Surgery* 88:507 (1980); Saudek et al., *N. Engl. J. Med.* 321:574 (1989)). In another embodiment, polymeric materials can be used (et, al., *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.* 23:61 (1983); Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, thus requiring only a fraction of the systemic dose (see e.g., Goodson, in *Medical Applications of Controlled Release*, supra, Vol. 2, pp. 115–138 (1984)). Other controlled release systems are discussed in, for example, the review by Langer (*Science* 249:1527–1533 (1990)).

The present invention also provides pharmaceutical compositions for administering Ang-7 compounds. Such compositions comprise a therapeutically effective amount of an Ang-7 compound and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more typically in humans. The term "carrier" refers to a diluent, adjuvant, excipient, stabilizer, or vehicle with which the Ang-7 compound is formulated for administration.

A pharmaceutically acceptable carrier can contain a physiologically acceptable compound that acts, for example, to stabilize the composition or to increase or decrease the absorption of the agent. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Carriers further include sterile liquids, such as water and oils, including those of petroleum, animal, vegetable or synthetic origin, such as peanut oil, soybean oil, mineral oil, sesame oil, and the like. Water is a typical carrier when the pharmaceutical composition is administered intravenously. Saline solutions and aqueous dextrose and glycerol solutions can also be employed as liquid carriers, particularly for injectable solutions. Various preservatives are well known and include, for example, phenol and ascorbic acid. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. One skilled in the art would know that the choice of a pharmaceutically acceptable carrier, including a physiologically acceptable compound, depends, for example, on the route of administration of the polypeptide and on the particular physiochemical characteristics of the specific polypeptide. For example, a physiologically acceptable carrier such as aluminum monosterate or gelatin is particularly useful as a delaying agent, which prolongs the rate of absorption of a pharmaceutical composition administered to a subject. Further examples of carriers, stabilizers or adjutants can be found in Martin, *Remington's Pharm. Sci.*, 15th Ed. (Mack Publ. Co., Easton, 1975), incorporated herein by reference. The pharmaceutical composition also can be incorporated, if desired, into liposomes, microspheres or other polymer matrices (See Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

When practiced in vivo, methods of administering a pharmaceutical composition containing the vector of this invention, are well known in the art and include but are not limited to, administration orally, intra-tumorally, intravenously, intramuscularly or intraperitoneal. Administration can be effected continuously or intermittently and will vary with the subject and the condition to be treated, for example, as is the case with other therapeutic compositions (see Landmann et al., *J. Interferon Res.* 12:103–111 (1992); Aulitzky et al, *Eur. J. Cancer* 27:462–67 (1991); Lantz et al., *Cytokine* 2:402–06(1990); Supersaxo et al., *Pharm. Res.* 5:472–76(1988); Demetri et al., *J. Clin. Oncol.* 7:1545–53 (1989); and LeMaistre et al., *Lancet* 337:1124–25 (1991)).

Pharmaceutical compositions can take the form of solutions, suspensions, emulsion, tablets, pills, capsules, powders, sustained-release formulations, and the like. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Pharmaceutical compositions will contain a therapeutically effective amount of the Ang-7 compound, typically in purified form, together with a suitable amount of carrier so as to provide a formulation proper for administration to the patient. The formulation should suit the mode of administration.

In one embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic to ease pain at the site of the injection. Generally, the ingredients are supplied either separately or mixed together in unit dosage form. For example, as a dry lyophilized powder or water-free concentrate in a hermetically sealed container such as an ampoule or sachette indicating the quantity of Ang-7 compound. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The Ang-7 compounds can be formulated as neutral or salt forms. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

The amount of the Ang-7 compound that will be effective in the treatment of a particular disorder or condition as indicated by modulation of angiogenesis will depend on the nature of the disorder or condition, and can be determined by standard clinical techniques. In addition, in vitro assays can optionally be employed to help identify optimal dosage ranges. The precise dose of the Ang-7 compound to be employed in the formulation will also depend on the route of administration, and the seriousness of the disease or disorder, and should be decided according to the judgment of the practitioner and each patient's circumstances. Suitable dosage ranges for intravenous administration are generally about 20–500 micrograms of active Ang-7 compound per kilogram body weight. Suitable dosage ranges for intranasal administration are generally about 0.01 pg/kg body weight to 1 mg/kg body weight. Effective doses can be extrapolated from dose response curves derived from in vitro or animal model test systems. Suppositories generally contain active ingredient in the range of 0.5% to 10% by weight; oral formulations typically contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Treatment of Angiogenesis-Related Diseases

In another embodiment, Ang-7 compounds, such as Ang-7 polypeptides, or fragments, variants, derivatives or analogs thereof, or ANG-7 nucleic acids encoding such polypeptides, can be used to treat diseases or clinical conditions that may be related to angiogenesis. Without intending to be bound by any particular theory, it is believed that the initiation and/or progression of many diseases is dependent on angiogenesis. For example, tumor formation is closely associated with angiogenesis. Such tumors include solid tumors, such as rhabdomyosarcomas, retinoblastoma, Ewing sarcoma, neuroblastoma, and osteosarcoma, and benign tumors, such as acoustic neuroma, neurofibroma, trachoma and pyogenic granulomas. Thus, tumor formation or progression can be treated by inhibiting angiogenesis; administering Ang-7 polypeptides, fragments, variants, derivatives and analogs, or ANG-7 nucleic acids, to the tumor will inhibit further tumor growth and/or progression. Similarly, cells expressing recombinant Ang-7 polypeptides, fragments or variants can be used. Alternatively, decreased angiogenesis is associated with cardiovascular disease. Thus, Ang-7 compounds that increase angiogenesis can be used to treat angiogenesis. Any of the methodologies described above can be applied to the treatment of such angiogenesis-related diseases.

Other diseases or clinical conditions involving unwanted angiogenesis can also be treated in a similar manner. Such other diseases or conditions include, but are not limited to, ocular neovascular disease, age-related macular degeneration, diabetic retinopathy, corneal graft rejection, neovascular glaucoma and retrolental fibroplasia, epidemic keratoconjunctivitis, Vitamin A deficiency, contact lens overwear, atopic keratitis, superior limbic keratitis, pterygium, keratitis sicca, Sjogren's syndrome, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarthritis, Wegener's sarcoidosis, Scleritis, Steven's Johnson disease, periphigoid radial keratotomy, corneal graph rejection, sickle cell anemia, sarcoidosis, syphilis, pseudoxanthoma elasticum, Pagets disease, vein occlusion, artery occlusion, carotid obstructive disease, chronic uveitis/vitreitis, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargart's disease, pars planitis, chronic retinal detachment, hyperviscosity syndromes, toxoplasmosis, trauma and post-laser complications. Other diseases include those associated with rubeosis, abnormal proliferation of fibrovascular or fibrous tissue, rheumatoid arthritis, osteoarthritis, ulcerative colitis, Crohn's disease, Bartonellosis, atherosclerosis, hemangioma, Osler-Weber-Rendu disease, hereditary hemorrhagic telangiectasia, and leukemia.

Antisense Regulation of ANG-7 Expression:

In a specific embodiment, Ang-7 function is inhibited by use of ANG-7 antisense nucleic acids. The present invention provides for the administration of nucleic acids of at least six nucleotides that are antisense to a gene or cDNA encoding Ang-7 polypeptide or a fragment or variant thereof to inhibit the function of Ang-7 polypeptide. An ANG-7 "antisense" nucleic acid as used herein refers to a nucleic acid that hybridizes to a portion of an ANG-7 RNA (typically mRNA) by virtue of some sequence complementarity. The antisense nucleic acid can be complementary to a coding and/or noncoding region of an ANG-7 mRNA. Absolute complementarity, although typical, is not required, however. A sequence "complementary to at least a portion of an RNA," as referred to herein, means a sequence having sufficient complementarity to be able to hybridize with the RNA, forming a stable duplex. In the case of double-stranded ANG-7 antisense nucleic acids, a single strand of the duplex DNA can be tested, or triplex formation can be assayed. The ability to hybridize will depend on both the degree of complementarity and the length of the antisense nucleic acid. Generally, the longer the hybridizing nucleic acid, the more base mismatches it can contain and still form a stable duplex (or triplex, as the case may be). One skilled in the art can ascertain a tolerable degree of mismatch by use of standard procedures to determine the melting point of the hybridized complex.

Such antisense nucleic acids have utility as agents that inhibit Ang-7 function, and can be used in the treatment or prevention of diseases or clinical conditions, as described supra. The antisense nucleic acids of the invention can be oligonucleotides that are double-stranded or single-stranded, RNA or DNA, or a derivative thereof, which can be directly administered to a cell, or which can be produced intracellularly by transcription of exogenous, introduced nucleic acid sequences.

In a specific embodiment, the ANG-7 antisense nucleic acid provided by the instant invention can be used to prevent angiogenesis. The invention further provides pharmaceutical compositions comprising an effective amount of the ANG-7 antisense nucleic acids of the invention in a pharmaceutically acceptable carrier, as described supra. In another embodiment, the invention is directed to methods for inhibiting the expression of an ANG-7 nucleic acid sequence in a eukaryotic cell comprising providing the cell with an effective amount of a composition comprising an ANG-7 antisense nucleic acid of the invention. ANG-7 antisense nucleic acids and their uses are described in detail below.

The ANG-7 antisense nucleic acids are of at least six nucleotides and are typically oligonucleotides (ranging from 6 to about 50 nucleotides or more). In specific aspects, the oligonucleotide is at least 10 nucleotides, at least 15 nucleotides, at least 100 nucleotides, or can be at least 200 nucleotides. The oligonucleotides can be DNA or RNA or chimeric mixtures or derivatives thereof, and can be single-stranded or double-stranded. A derivative can be modified at the base moiety, sugar moiety, or phosphate backbone, as described below. The derivative can include other appending groups such as peptides, or agents facilitating transport across the cell membrane (see e.g., Letsinger et al., *Proc. Natl. Acad. Sci. USA* 86:6553–56 (1989); Lemaitre et al., *Proc. Natl. Acad. Sci. USA* 84:648–52 (1987); International Patent Publication WO 88/09810) or blood-brain barrier (see, e.g., International Patent Publication WO 89/10134), hybridization-triggered cleavage agents (see, e.g., Krol et al., *BioTechniques* 6:958–76 (1988)) or intercalating agents (see, e.g., Zon, *Pharm. Res.* 5:539–49 (1988)).

In one embodiment of the invention, a ANG-7 antisense oligonucleotide is provided, typically as single-stranded DNA. The oligonucleotide can be modified at any position on its structure with substituents generally known in the art. The ANG-7 antisense oligonucleotide can comprise at least one modified base moiety, such as, for example, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylamino-methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, 2,6-diaminopurine, and the like. In another embodiment, the oligonucleotide comprises at least one modified sugar moiety, such as, for example, arabinose, 2-fluoroarabinose, xylulose, and hexose.

In yet another embodiment, the oligonucleotide comprises at least one modified phosphate backbone, such as, for example, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (see Gautier et al., *Nucl. Acids Res.* 15:6625–41 (1987)). The oligonucleotide can be conjugated to another molecule (e.g., a peptide, hybridization triggered cross-linking agent, transport agent, hybridization-triggered cleavage agent, and the like).

Oligonucleotides of the invention can be synthesized by standard methods known in the art (e.g., by use of a commercially available automated DNA synthesizer). As examples, phosphorothioate oligonucleotides can be synthesized by the method of Stein et al. (see *Nucl. Acids Res.* 16:3209 (1988)), and methyphosphonate oligonucleotides can be prepared by use of controlled pore glass polymer supports (see Sarin et al., *Proc. Natl. Acad. Sci. USA* 85:7448–51 (1988)), and the like.

In a specific embodiment, the ANG-7 antisense oligonucleotide comprises catalytic RNA, or a ribozyme (see, e.g., International Patent Publication WO 90/11364; Sarver et al., *Science* 247:1222–25 (1990)). In another embodiment, the oligonucleotide is a 2'-0-methylribonucleotide (see e.g., Inoue et al., *Nucl. Acids Res.* 15:6131–48 (1987)), or a chimeric RNA-DNA analogue (see e.g., Inoue et al, *FEBS Lett.* 215:327–30 (1987)).

In an alternative embodiment, the ANG-7 antisense nucleic acid of the invention is produced intracellularly by transcription from an exogenous sequence. For example, a vector can be introduced in vivo such that it is taken up by a cell, within which the vector or a portion thereof is transcribed, producing an antisense nucleic acid (RNA) of the invention. The vector would contain a sequence encoding the ANG-7 antisense nucleic acid or a portion thereof. Once inside the cell the vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art and used for replication and expression in mammalian cells. Expression of the sequence encoding the ANG-7 antisense RNA can be controlled by any promoter known in the art to act in mammalian, typically human, cells. The promoters can be inducible or constitutive. Inducible promoters include but are not limited to, the SV40 early promoter region (see Bernoist and Chambon, Nature 290:304–10 (1981)), the promoter contained in the 3' long terminal repeat of Rous sarcoma virus (see Yamamoto et al., Cell 22:787–97 (1980)), the herpes thymidine kinase promoter (see Wagner et al., Proc. Natl. Acad. Sci. USA 78:1441–45(1981)), the regulatory sequences of the metallothionein gene (see Brinster et al., Nature 296:39–42 (1982)), and the like.

Animal Models:

The invention also provides animal models. In one embodiment, animal models for diseases and disorders involving angiogenesis are provided. Such an animal can be initially produced by promoting homologous recombination between an ANG-7 gene in its chromosome and an exogenous ANG-7 gene that has been rendered biologically inactive (typically by insertion of a heterologous sequence, such as an antibiotic resistance gene). For example, homologous recombination is carried out by transforming embryo-derived stem (ES) cells with a vector containing the insertionally inactivated ANG-7 gene, such that homologous recombination occurs, followed by injecting the ES cells into a blastocyst, and implanting the blastocyst into a foster mother, followed by the birth of the chimeric animal ("knockout animal") in which an ANG-7 gene has been inactivated (see, e.g., Capecchi, Science 244:1288–1292 (1989); U.S. Pat. Nos. 5,631,153; 5,627,059; 5,487,992; and 5,464,764). The chimeric animal can be bred to produce additional knockout animals. Such animals can be mice, hamsters, sheep, pigs, cattle, and the like, and are typically non-human mammals. In a specific embodiment, a knockout mouse is produced. Knockout animals are expected to develop or be predisposed to developing diseases or disorders associated with hyper-angiogenic conditions and can be useful to screen for or test molecules for the ability to decrease angiogenesis and thus treat or prevent such diseases and disorders.

In another embodiment, transgenic animals that have incorporated and overexpress ANG-7 genes have use as animal models of diseases and disorders involving hypo-angiogenesis. Transgenic animals are expected to develop or be predisposed to hypo-angiogenic conditions, or exhibit increased resistance to diseases requiring angiogenesis, such as tumor formation. Thus, these animals can have use as animal models of such diseases and disorders, or the resistance to such diseases and conditions.

EXAMPLES

The following examples are offered to illustrate, but no to limit the claimed invention.

Example 1

To identify members of the angiopoietin ligand family, a BLAST search (Altschul et al., Nucleic Acids Res. 25:3389–402 (1997)) was performed using the Expressed Sequence Tag (EST) database from the National Center for Biotechnology Information (NCBI). The amino acid sequence of Ang-1 was used as a probe. This search identified a human EST (Accession Number AA773234). The corresponding amino acid sequence of this EST showed significant sequence identity in the +2 reading frame to Ang-1. The probability (P) value was $4.4 \times 10^{-28}$, which strongly indicates that the identified EST encodes a fragment of a protein which belongs to the family of angiopoietins. Further proof that the EST encodes a fragment of an angiopoietin protein (which was designated as "Ang-7") was obtained when a BLAST search of a Swissprot database was performed using the deduced amino acid sequence of EST AA773234). The P values obtained for alignments of Ang-1 and Ang-2 with the partial amino acid sequence of Ang-7 were $3.2 \times 10^{-32}$ and $2.6 \times 10^{-34}$, respectively.

A further search of the EST database identified another EST (Accession Number AA255590), which also encoded a portion of the ANG-7 cDNA. DNA sequence analysis revealed that the nucleotide sequence of EST AA255590 overlaps a portion of the sequence of EST AA773234. Because EST AA773234 was not readily available, the EST AA255590 nucleic acid was used as a probe in subsequent experiments.

Example 2

To obtain the full-length cDNA clone encoding Ang-7, EST AA255590 was used to probe a human cDNA library. Briefly, EST AA255590 is located in vector pT7T3D-Pac (Pharmacia, Peapack, N.J.) between the Not I and Eco RI restriction endonuclease sites. The plasmid was linearized with the restriction endonuclease EcORI. An antisense [$^{32}$P] radioactively labeled RNA probe was generated using a Strip-EZ T3 kit (Ambion, Austin, Tex.), in accordance with the manufacturer's instructions. A Human Universal cDNA Library (HUCL) was screened by hybridizing HUCL primary membranes (Stratagene, La Jolla, Calif., USA) with the radioactively-labeled RNA probe. Hybridization and washing were performed as recommended by the manufacturer. (See Strip-EZ Kit Manual). After washing, the membrane was exposed to a phosphorimager screen, scanned on a Fuji Bas-1500 scanner, and the intensity of the radioactive signals was evaluated with the TINA 2.0 software (Raytest, Straubenhardt, Germany). Analysis of the hybridization profile revealed a signal at the position L04. The corresponding secondary array membrane was hybridized under the same conditions. A hybridization signal was detected at position G19 on the secondary array membrane. The individual clone L04G19 was obtained from the supplier. Analysis of the L04G19 clone revealed that it contained an insert of about 2.2 kilobases ("kb"). DNA sequence analysis confirmed that this cDNA clone contained the full length coding sequence of the ANG-7 cDNA.

Example 3

DNA sequence analysis of the L04G19 cDNA revealed that the cDNA is 2,173 base pairs ("bp") long., which includes a short poly A tail. The ANG-7 cDNA sequence is shown in FIG. 1 (SEQ ID NO:1). The cDNA has an open reading frame of 1,432 bp. The open reading frame encodes a polypeptide of 493 amino acid residues (SEQ ID NO:2; FIG. 2). A similarity alignment of the amino acid sequence of Ang-7 with the sequences of human angiopoietin-I (SEQ ID NO:3), human angiopoietin-2 (SEQ ID NO:4), human angiopoietin-3 (SEQ ID NO:5) and human angiopoietin-4

Figure 3:
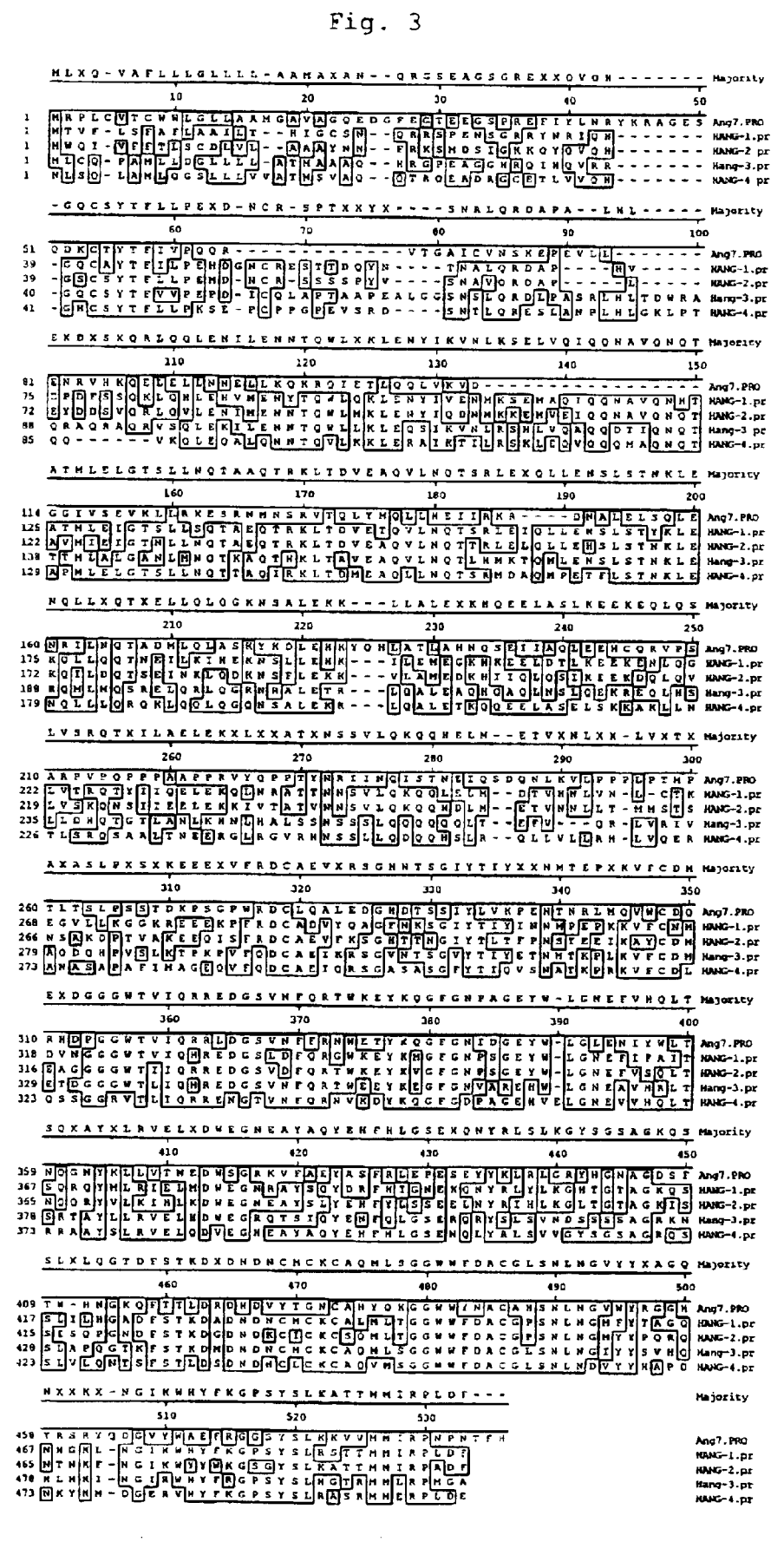

(SEQ ID NO:6) was conducted using the MEGALIGN™ Expert Sequence Analysis Software in the LASERGENE™ software package (DNASTAR, Madison, Wis.). Referring to FIG. 3, the N-terminal and C-terminal portions of Ang-7 polypeptide contain characteristic coiled-coil and fibrinogen-like domains, which are also found in other angiopoietins. The overall similarity index between the Ang-7 polypeptide and Ang-1 and -2 polypeptides is 23.9% and 23.5%, respectively. Importantly, most of the amino acid residues which are conserved between the known angiopoietins are also present in the Ang-7 (See FIG. 3). This amino acid sequence conservation confirms that the L04G19 cDNA clone encodes a member of the angiopoietin family.

Example 4

Figure 4:
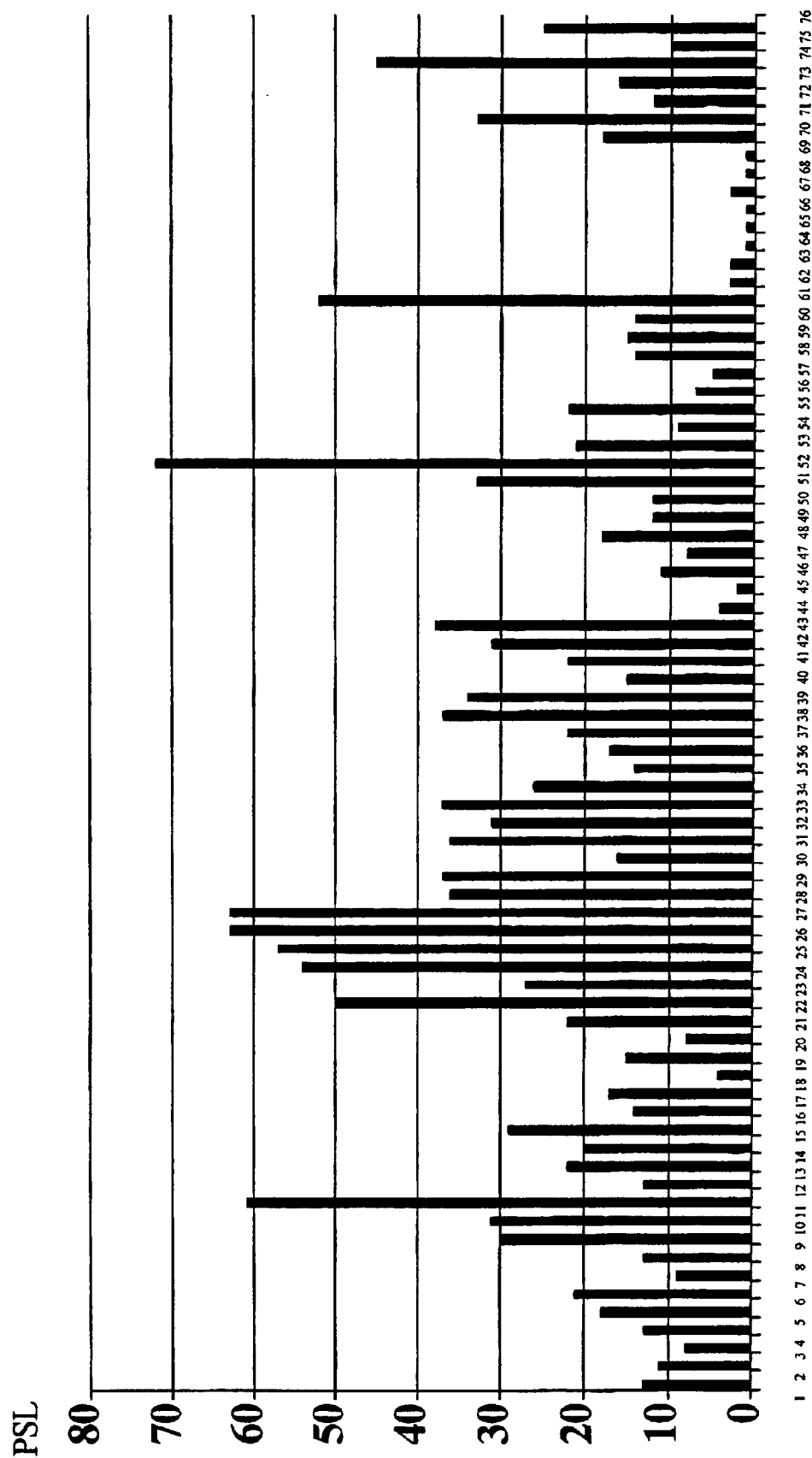
FIG. 4 depicts an expression profile of ANG-7 RNA in human tissues. The expression levels of ANG-7 RNA in different tissues is shown. Along the horizontal axis, the reference numerals identify the following tissues.

The tissue expression profile of the ANG-7 gene was examined. Briefly, the plasmid encoding EST AA255590 was linearized with restriction endonuclease EcORI. An antisense [$^{32}$P]-radioactively-labeled RNA probe was generated using a Strip-EZ T3 kit (Ambion, Austin, Tex., USA), in accordance with the manufacturer's instructions. A human multiple tissue expression array (Clontech Laboratories, Inc., Palo Alto, Calif., USA) was hybridized with the radioactively labeled RNA probe. Hybridization and washing were performed as recommended in the Strip-EZ Kit Manual. After washing, the membrane was exposed to a phosphorimager screen, scanned on a Fuji Bas-1500 scanner, and the intensity of the radioactive signals was evaluated with the TINA 2.0 software (Raytest, Straubenhardt, Germany). The resulting histogram is presented on FIG. 4 and demonstrates that the ANG-7 RNA is strongly expressed in heart tissues (atrium left and right, ventricle left and right), uterus, mammary gland and corpus callosum tissues. Expression of the ANG-7 RNA in these tissues, which are heavily vascularized, indicates that Ang-7 polypeptide, like Ang-1 and -2 polypeptide, could play a role in angiogenesis.

Example 5

To test whether the ANG-7 cDNA is translated into Ang-7 polypeptide and to determine the molecular weight of the Ang-7 polypeptide, the ANG-7 cDNA was amplified by polymerase chain reaction ("PCR"). For PCR amplification, a 5' primer (5' GCGAATTCACCATGAGGCCACTGT-GCGT 3' (SEQ ID NO:7)), which is complementary to the 5' end of the ANG-7 cDNA, was used in combination with a 3' primer (5' GGAAGCTTATGGAAGGTGTTGGGGT-TCGG 3' (SEQ ID NO:8)), which is complementary to the 3' end of the ANG-7 cDNA. To increase translational efficiency, a Kozak translation initiation consensus sequence was also included in the 5' primer. To facilitate subsequent cloning of the PCR fragment, restriction recognition sequences for the restriction enzymes Eco RI and Hind III were introduced into the 5' and 3' primers, respectively. The amplified cDNA was cloned into the Eco RI and Hind III restriction sites of the mammalian expression vector pcDNA3.1/Myc-His(-) (Invitrogen, Groningen, Netherlands) to create pcDNA3.1/ang7/mychis.

ANG-7 RNA transcripts were synthesized from the T7 promoter of pcDNA3.1/ang7/mychis, according to the manufacturer's instructions. In vitro translation was conducted using a rabbit reticulocyte lysate, according to the manufacturer's instructions (Promega, Madison, Wis., USA). The resulting proteins produced by in vitro translation were labeled using [$^{35}$S]methionine. The labeled proteins were separated by electrophoresis on a sodium dodecyl sulfate-12% polyacrylamide gel and visualized by autoradiography. FIG. 5 depicts the results of this experiment. Specifically, Lane 1: Rainbow [$^{14}$C]methylated protein molecular weight marker (Amersham, Little Chalfont Buckinghamshire, England) which included the following proteins: ovalbumin (46 kDa), carbonic anhydrase (30 kDa), trypsin inhibitor (21.5 kDa), lysozyme (14.3 kDa), and aprotinin (6.5 kDa). Lane 2 contained in vitro translation products of ANG-7 RNA using the T7 promoter of the mammalian expression vector pcDNA3.1/Myc-His(-) (Invitrogen, Groningen, Netherlands). Lane 3 contained the in vitro translation products using the SP6 promoter of the mammalian expression vector pcDNA3.1/Myc-His(-) (negative control). Lane 4 contained a positive control from the in vitro translation system (Promega, Madison, USA).

A major band of 60 kilodaltons was detected. The observed molecular mass of the major band was slightly larger than the calculated molecular mass of recombinant Ang-7 polypeptide (57.1 kDa). This difference may be explained by glycosylation of several potential glycosylation sites in the Ang-7 polypeptide.

Example 6

To determine whether ANG-7 cDNA can be expressed recombinantly in vivo in eukaryotic cells, the ANG-7 cDNA was cloned into three eukaryotic expression vectors, and subsequently transfected into tissue culture cells.

The ANG-7 cDNA was cloned into the expression vector pcDNA3.1/Myc-His(-) (Invitrogen, Catalog No. V85520), as described above. ANG-7 cDNA was also cloned into pIRES (Clontech, Catalog No. 6060-1) and pZeo (Invitrogen, Catalog No. V850-01)). To facilitate detection and purification, a polyhistidine tag was included in the C-terminal coding region of each expression unit.

The expression constructs were transfected into Chinese Hamster Ovary ("CHO") cells using the DOS PER liposomal transfection reagent (Boehringer Mannheim, Catalog No. 1781995). Briefly, 0.5×10$^6$ CHO cells were seeded into each well of a 6-well plate in basal medium (DMEM, Gibco/BRL, Catalog No. 41965-039); 2 mM L-Glutamine (Gibco/BRL, Catalog No. 25030-024), Penicillin/Streptomycin (1500 IU/ml) (Gibco/BRL, Catalog No. 15140-114), and 10% Fetal Bovine Serum (FBS, Sigma, Catalog No. F2442)). After overnight incubation at 37° C., the medium was discarded, and 500 µl of basal medium (without FBS) was mixed with 5 µg of DNA and 25 µl of DOSPER were added to each well. The plates were incubated for 15 min at room temperature and then an additional 520 µl well of the basal medium (without FBS) was added. The cells were incubated for an additional 3 hours at 37° C. After the incubation, an additional 3 ml/well of basal medium was added. The next day, the medium was discarded, and 3 ml/well of fresh basal was medium added. The cells were incubated for additional two days, harvested, and then the cytoplasmic expression of the Ang-7 polypeptide was analyzed in a Western blot using Tetra-His antibodies (Qiagen, Catalog No. 34670). The Western blot was performed according to the manufacturer's instructions, and contained thee lanes. Lane 1 contained the protein molecular weight markers; Lane 2 contained media from CHO cells (negative control); and Lane 3 contained the transiently transfected CHO cells expressing Ang-7 polypeptide. The Western blot analysis is shown in FIG. 6, where the Ang-7 polypeptide band is marked by an arrow. A band of about 57 kDa was observed in CHO cells transfected with the ANG-7 cDNA, but not in the cells transfected with the vector alone.

(Compare lanes 2 and 3.) Thus, ANG-7 cDNA was transiently expressed in mammalian cells and produced a polypeptide of the expected molecular weight.

Example 7

To generate cell clones stably expressing recombinant Ang-7 polypeptide, ANG-7 cDNA clones were transfected into a human line and then stable transfectants were selected. Briefly, a human embryonic kidney cell line, HEK293, was transfected with expression vectors pcDNA3.1/ang7/mychis or pIRES containing the ANG-7 cDNA under the control of the *Cytomegalovirus* promoter. Transfection was performed as described above in Example 6. Following transfection, the cells were seeded into 96 well plates and cultured in selection media (Basal medium plus 0.75 mg/ml Geneticin (Gibco/BRL, Catalog No. 10131-027)).

Recombinant expression of Ang-7 was detected by immunofluorescent staining on Lab-Tek chamber slides (Nalgene Nunc, Catalog No. 154534) using a Tetra-His antibody (Qiagen, Catalog No. 34670) and FITC labeled secondary antibody (Goat anti mouse IgG-FITC conjugate (Dianova, Catalog No. 115-095-062)). About $4 \times 10^4$ cells were seeded per well of the Lab-Tek slide and incubated overnight in a $CO_2$ incubator. The medium was discarded, and the cells were washed once with PBS (PBS Dulbecco's w/o Calcium/ Magnesium/Sodium bicarbonate (Gibco/BRL, Catalog No. 14190-094)). The cells were then fixed by addition of 200 μl/well of ice-cold methanol and incubation at −20° C. for 10 min. After fixation, the cells were washed 2× with PBS containing 3% BSA (PBS-BSA), and then blocked for 30 min by PBS-BSA at 37° C. Following blocking, 100 μl/well of a 1:50 dilution of the Tetra-His antibody in PBS-BSA was added. The slides were incubated for 2 hours at 37° C. After incubation with the primary antibody, the cells were washed 10× with PBS and then 100 μl/well of a 1:100 dilution of the secondary antibody (Goat anti mouse IgG-FITC conjugate) was added. The slides were incubated for 1 hour at 37° C. The slides were washed 10× with PBS, the well separating grid was removed, and then the slides were covered with the anti-fading mounting medium ROTI$^R$Histokit (Carl Roth, Catalog No. 6638.1) and a cover glass. After hardening of the mounting medium (usually overnight), the slides were observed in a fluorescent microscope. Positive clones were expanded into 24-well plates, and the expression level of recombinant protein was compared by analyzing cell lysates on a western blot as described above in Example 6. The Western blot analysis is depicted in FIG. 7. Lane 1 of the Western blot contained the protein molecular weight markers; Lane 2 contained media from HEK293 cells (negative control); and Lane 3 contained stably transfected HEK293 cells expressing Ang-7 polypeptide. Positive clones were selected for further analysis, as described below.

The Ang-7 polypeptide has a secretion signal on its N-terminus, which suggests that it is a secreted protein. To determine whether recombinantly expressed Ang-7 polypeptide is secreted by cells, conditioned media from a stably transfected HEK293 cell clone, number 62, was analyzed for the presence of Ang-7 polypeptide. Briefly, the protein was partially purified from conditioned media using a Ni-NTA agarose resin (Qiagen, # 304050), as more fully described in Example 8. The eluted column fractions were analyzed on a Western blot, as described above. The Western blot analysis is depicted in FIG. 8. Lane 1 of the Western blot contained conditioned media from a HEK293 cells (negative control); and Lane 2 contained conditioned media from the stably transfected HEK293 cell clone expressing Ang-7 polypeptide.

Referring to FIG. 8, conditioned medium from the stably transfected HEK293 cell line contained a polypeptide that reacted with the Tetra-His antibody, while conditioned media from untransformed HEK293 cells lacked such a cross-reacting polypeptide. This experiment confirms that Ang-7 polypeptide is a secreted into the media.

Example 8

To further characterize the Ang-7 polypeptide, it was purified from conditioned culture media using Ni-NTA resin (Qiagen, # 304050). Briefly, conditioned media from clone 62 was collected after three days. One tablet of "complete" proteinase inhibitor ("Complete" proteinase inhibitor cocktail tablets; Boehringer Mannheim (Roche Diagnostics) Catalog No. 1697498) was added to each 50 ml of collected media. Afterwards, imidazole (Sigma; Catalog No. I-2399) was added to a final concentration of 8 mM. The media was centrifuged for 10 min at 1600×g. The supernatant was transferred to fresh tubes, and 500 μl of 50% slurry of Ni-NTA agarose was added to each 50 ml of medium. The tubes were gently rocked at 4° C. for 60 min. The Ni-NTA resin was collected by centrifugation at 1600×g for 10 min, and the supernatant was discarded. The resin was washed twice with wash buffer (50 mM $NaH_2PO_4$, pH 8.0; 300 mM NaCl; 10 mM Imidazole) by suspending the resin in the washing buffer followed by centrifugation under the same conditions. After washing, the resin was again resuspended in wash buffer and transferred to a 1 ml column (0.5–1 ml resin bed per column). Bound Ang-7 polypeptide was eluted in four 500 μl portions using elution buffer (50 mM $NaH_2PO_4$, pH 8.0; 300 mM NaCl; 250 mM Imidazole). The fractions were analyzed by Western blotting using the Tetra-His antibody, as described above. The Western blot analysis is depicted in FIG. 9A. The purity of the isolated protein was analyzed on a Coomassie-stained SDS gel, and this analysis is depicted in FIG. 9B.

Referring to FIG. 9A, Western blotting revealed a doublet of bands at about 62–64 kDa. Comparison of the Western blot analysis with the coomassie-stained SDS gel revealed a corresponding doublet of the same molecular weights. (Compare FIGS. 9A and 9B). The presence of the doublet of Ang-7 polypeptides suggests that different glycosylated forms of Ang-7 are secreted by stably transfected cells.

Example 9

The effect of ANG-7 gene expression on endothelial tube formation was determined by examining HUVEC capillary like-organization in Matrigel. Adenovirus expression vectors containing ANG-7 cDNA were constructed by excising ANG-7 cDNA from pcDNA3.1/ang7/mychis by digestion with Eco RV and Pme1. The resulting fragment was cloned into the corresponding sites of pShuttle-CMV (He et al., *Proc. Nat. Acad. Sci. USA* 95:2509–14 (1998)). pShuttle-CMV is an adenovirus shuttle vector in which the transgene (i.e., ANG-7 cDNA) is under the control of the *cytomegalovirus* ("CMV") promoter. This construct was transferred to an adenoviral backbone by recombination in *E. coli* with the plasmid pAdEasy ("AdEZ") (He et al., supra). The resulting recombinant was linearized with the restriction endonuclease Pac 1 and then transfected into HEK293 cells (Microbix Inc, Ontario, Canada) by standard methods. Ten days post-transfection (after the appearance of viral plaques), vector particles were harvested from the cells by multiple rounds of freeze-thawing. Particles were then used to infect 911 epithelial cells (Introgene, Leiden, Netherlands). To obtain sufficient vector for multiple experiments, three rounds of passage of viral particles to successively larger cultures of 911 cells were performed. This viral stock was termed "Ad-Ang7." This crude stock was used in the following experiment.

HUVEC were plated at $1.25 \times 10^4$ cells per well at day zero in a 24 well plate. The cells were infected with Ad-Ang7 stock, with the control vector Ad-Ez, or with an Ad-VEGF stock (Vascular Endothelial Growth Factor). 200 μl of each viral stock was added to the wells on day 0. The plates were incubated in 5% $CO_2$ at 37° C. for 5 days. On day 6, the cells were passed to a 24 well plate coated with Matrigel at a density of $3 \times 10^4$ cells/well. The Matrigel coated plates were prepared as follows: Matrigel basement membrane matrix (Becton Dickinson) was thawed on ice overnight at 4° C. Pre-cooled pipettes, pipette tips, plates and tubes where used. 0.3 μl/well of Matrigel (at 4° C.) was used to coat the wells of a 24 well plate. The Matrigel was polymerized at 37° C. for 2 hours. Following addition of HUVEC to the Matrigel coated wells, the plates was incubated for 24 hours at 5% $CO_2$ and 37° C. All tests were performed in triplicate wells. The final volume in each well is 1 ml.

After 24 hours, incubation at 37° C., 5% $CO_2$, each well was checked under a microscope at low magnification (inverted microscope at ×10 power). The plates were then stained with Diff-Quick, and pictures were be taken to compare the controls with the different concentrations.

The following tables summarize the protocol.

TABLE 1

No Matrigel

| No Matrigel treatment (5 days) | Volume | Medium Volume |
| --- | --- | --- |
| 1. HUVEC Control (6 wells) | 0 | 1 ml. |
| 2. 911 Sup. plus cell Lysate | 200 μl. | 800 μl. |
| 3. Ad-EZ plus cell lysate | 200 μl | 800 μl |
| 4. Ad-VEGF plus cell Lysate | 200 μl. | 800 μ. |
| 5. Ad-Ang7 plus cell Lysate | 200 μl. | 800 μl. |

TABLE 2

Matrigel Treatment

| Matrigel Treatment (Day 6) | Volume | Medium Volume |
| --- | --- | --- |
| 1. HUVEC Control | 0 | 1 ml. |
| 2. 911 Sup. plus cell lysate | 200 μl. | 800 μl. |
| 3. Ad-EZ plus cell lysate | 200 μl | 800 μl |
| 4. Ad-VEGF plus cell lysate | 200 μl. | 800 μl. |
| 5. Ad-Ang7 plus cell lysate | 200 μl. | 800 μl. |

The results were as follows, where the length of the tubing formation is given in centimeters. (SEM indicates standard error of the mean.)

TABLE 3

Endothelial Tubing Formation

| Condition | Control | 911 Lys. | Ad-EZ | Ad-VEGF | Ad-Ang7 |
| --- | --- | --- | --- | --- | --- |
| Well 1 | 68.22 | 82 | 60.8 | 78.6 | 35 |
| Well 2 | 81.4 | 88.8 | 63.2 | 69.6 | 31.8 |
| Well 3 | 70.56 | 75.2 | 89.4 | 68.8 | 36.2 |
| Avg. | 73.39 | 82.00 | 71.13 | 72.33 | 34.33 |
| SEM | 4.06 | 4.81 | 9.16 | 3.14 | 1.31 |

As can be seen from this example, the control cells and cells infected with the vector alone (Ad-EZ) showed similar amounts of tubing formation. Expression of VEGF also produced similar levels of tubing formation. In contrast, expression of Ang-7 polypeptide markedly inhibited tubing formation. Thus, this experiment demonstrates that Ang-7 polypeptide inhibits angiogenesis.

Example 10

The effect of in vivo expression of ANG-7 in B16 murine melanoma metastasis was examined. Briefly, the ANG-7 cDNA was delivered ex vivo with an adenoviral vector (Ad-Ang-7) followed by introduction of the transfected cells into mice. 74 females C 57 B1/6, 6–8 weeks old, were used. For ex vivo administration, either crude lysates (prepared as described above in Example 9) or purified vectors were used. The adenoviral vectors were purified as follows: The protocol is a modification of Fallux et al. (*Human Gene Therapy* 7:215–22 (1996)). For large scale purification, 911 cells were plated in a Multi-tray Cell Factory (Nuclon. Denmark). When the cells reached 85% confluence, they were infected with the recombinant adenovirus. Following infection, about 48–72 hours post-infection, when the cells showed a cytopathic effect, the cells were harvested and centrifuged. The cell pellet was resuspended in a small volume of medium, three cycles of freezing and thawing were performed, and the disrupted cells were pelleted to remove the cellular debris. The viral particle-containing supernatants were layered onto a discontinuous cesium chloride (CsCl) gradient composed of 1 ml at d=1.4 g/ml overlaid with 3 mls of d=1.25 g/ml. The gradients were centrifuged at 151,000×g for 2 hours. The opaque band of virus particles, at the 1.25/1.4 density boundary, was collected and loaded onto a homogeneous CsCl solution of d=1.3 g/ml. This second gradient was spun at 151,000×g for 18 hours. The single band of virus particles was collected and dialyzed twice for one hour against 0.135M NaCl, 1 mM $MgCl_2$, 10 mM Tris pH 7.5. The second and final dialysis was carried out against the same buffer with the addition of 10% glycerol. Stock titers were determined by plaque assay using 293 or 911 cells.

B16.F10 cells, from a murine melanoma metastasis were infected for 24 hours with one of the following adenovirus expression vectors: Ad-E1 (control), Ad-Ang7 or Ad-VEGF. The infected cells were injected intravenously into the lateral tail vein of the mice at the end of the 24 incubation period. The cell concentration of each injection was $2 \times 10^5$ cells in 0.2 ml of PBS. Day 0 was the date of injection into mice.

The animals were weighed two times a week. Two animals from group 1 (control) were sacrificed on day 14, the lungs collected and the number of metastases determined. Following counting of the metastases, the remainder of the animals (10 in each group) were sacrificed on day 14. At that time, lungs were collected, weighed and the number of metastases counted.

The following table summarizes the experimental protocol.

TABLE 4

| GROUP | NUMBER OF ANIMALS | CELL INFECTION | SACRIFICED ON |
| --- | --- | --- | --- |
| 1 | 10 | None | Day 14 (only 2 mice), |
| 2 | 10 | AdEZ | Day 14 |
| 6 | 9 | Ad-VEGF | Day 14 |
| 8 | 9 | Ad-Ang7 | Day 14 |

The following Table 5 summarizes the lung weights from each group. SEM is the "standard error of the mean."

TABLE 5

Lung Weight

| Group | Average | SEM | Median |
|---|---|---|---|
| 1 (control) | 200.4 | 63.4 | 203.2 |
| 2 (AdEz) | 219.0 | 69.3 | 222.5 |
| 6 (Ad-VEGF) | 173.3 | 61.3 | 172.6 |
| 8 (Ad-Ang7) | 168.6 | 56.2 | 168.6 |

The following Table 6 summarizes the number of lung metastases from each group. SEM is the "standard error of the mean."

TABLE 6

Lung Metastases

| Group | Average | SEM | Median |
|---|---|---|---|
| 1 (control) | 50.9 | 12.3 | 39.5 |
| 2 (AdEZ) | 24.3 | 7.1 | 27.7 |
| 6 (Ad-VEGF) | 48.3 | 10.0 | 47.1 |
| 8 (Ad-Ang7) | 3.0 | 2.1 | 0.0 |

As can be seen from this data, the average lung weight in mice receiving tumor cells overexpressing ANG-7 cDNA was markedly lower than in control animals. The average lung weight in AD-VEGF and Ad-Ang7 treated animals was similar. More importantly, and referring to Table 6, the average number of lung metastases was over 10 times less in tumor cells overexpressing Ang-7 polypeptide as compared with control and VEGF-treated animals. Thus, this data reveal that overexpression of ANG-7 cDNA inhibits tumor cell growth.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for inhibiting angiogenesis comprising administering to a mammal a therapeutically effective dose of an isolated Ang-7 polypeptide, wherein said polypeptide comprises SEQ ID NO:2.

2. The method of claim 1, wherein the mammal is human.

3. The method of claim 1, wherein the administering is performed in vivo.

4. The method of claim 1, further comprising administering a pharmaceutical carrier.

5. The method of claim 1, wherein the administering is ex vivo.

6. The method of claim 1, wherein the Ang-7 polypeptide is recombinantly expressed.

7. The method of claim 6, wherein the Ang-7 polypeptide is recombinantly expressed by culturing a cell containing an ANG-7 nucleic acid under conditions which result in expression of the polypeptide, and recovering the Ang-7 polypeptide from the cell culture.

8. The method of claim 6, wherein the Ang-7 polypeptide is expressed in *E. coli*.

9. The method of claim 6, wherein the Ang-7 polypeptide is expressed in mammalian cells.

10. The method of claim 7, wherein the ANG-7 nucleic acid is operably linked to a promoter in an expression vector.

11. The method of claim 7, wherein the ANG-7 nucleic acid has the sequence of human ANG-7 (SEQ ID NO:1).

12. A method of treating a tumor in a subject in need of anti-angiogenesis therapy comprising administering to a subject a therapeutically effective amount of an Ang-7 polypeptide, wherein said polypeptide comprises SEQ ID NO:2.

13. The method of claim 12, wherein the subject is human.

14. The method of claim 12, wherein the administering is performed in vivo.

15. The method of claim 12, further comprising administering a pharmaceutical carrier.

16. The method of claim 12, wherein the administration is ex vivo.

17. The method of claim 12, wherein the Ang-7 polypeptide is recombinantly expressed.

18. The method of claim 17, wherein the Ang-7 polypeptide is recombinantly expressed by culturing a cell containing an ANG-7 nucleic acid under conditions which result in expression of the polypeptide, and recovering the Ang-7 polypeptide from the cell culture.

19. The method of claim 17, wherein the Ang-7 polypeptide is expressed in mammalian cells, yeast cells, bacterial cells, or insect cells.

20. The method of claim 17, wherein the Ang-7 polypeptide is expressed in mammalian cells.

21. The method of claim 18, wherein the ANG-7 nucleic acid is operably linked to a promoter in an expression vector.

22. The method of claim 18, wherein the expression vector is an adenoviral vector, a retroviral vector, or a lentiviral vector.

23. The method of claim 18, wherein the ANG-7 nucleic acid has the sequence of human ANG-7 (SEQ ID NO:1).

24. A method of inhibiting endothelial tube formation comprising administering to an endothelial cell an effective amount of an Ang-7 polypeptide, wherein said polypeptide comprises SEQ ID NO:2.

25. A method of inhibiting tumor cell growth comprising administering to a tumor cell an effect amount of an Ang-7 polypeptide, wherein said polypeptide comprises SEQ ID NO:2.

26. A method of inhibiting tumor cell growth comprising administering to a tumor cell an effective amount of an Ang-7 polypeptide, or fragment, variant, derivative, analog or a pharmaceutically acceptable salt thereof.

27. The method of claim 26, wherein the Ang-7 polypeptide is human Ang-7.

* * * * *

SEQUENCE LISTING

```
<160> NUMBER OF SEQ ID NOS: 8

<210> SEQ ID NO 1
<211> LENGTH: 2173
<212> TYPE: DNA
<213> ORGANISM: Homo sapiens

<400> SEQUENCE: 1
gaaaatgagg ctgctgcgga cggcctgagg atgaacccca agccctggac ctgccgagcg     60
tggcactgag gcagcggctg acgctactgt gagggaaaga aggttgtgag cagccccgca    120
ggaccnctgg ccagccctgg ccccagcctc tgccggagcc ctctgtggag gcagagccag    180
tggagcccag tgaggcaggg ctgcttggca gccaccggcc tgcaactcag gaacccctcc    240
agaggccatg gacaggctgc cccgctgacg gccaggtgaa agcatgtgag gagccgcccc    300
ggagccaagc aggagggaag aggctttcat agattctatt cacaaagaat aaccaccatt    360
ttgcaaagac catgaggcca ctgtgcgtga catgctggtg gctcggactg ctggctgcca    420
tgggagctgt tgcaggccag gaggacggtt ttgagggcac tgaggagggc tcgccaagag    480
agttcattta cctaaacagg tacaagcggg cgggcgagtc ccaggacaag tgcacctaca    540
ccttcattgt gccccagcag cgggtcacgg gtgccatctg cgtcaactcc aaggagcctg    600
aggtgcttct ggagaaccga gtgcataagc aggagctaga gctgctcaac aatgagctgc    660
tcaagcagaa gcggcagatc gagacgctgc agcagctggt gaaggtggac ggcggcattg    720
tgagcgaggt gaagctgctg cgcaaggaga gccgcaacat gaactcgcgg gtcacgcagc    780
tctacatgca gctcctgcac gagatcatcc gcaagcggga caacgcgttg gagctctccc    840
agctggagaa caggatcctg aaccagacag ccgacatgct gcagctggcc agcaagtaca    900
aggacctgga gcacaagtac cagcacctgg ccacactggc ccacaaccaa tcagagatca    960
tcgcgcagct tgaggagcac tgccagaggg tgccctcggc caggcccgtc ccccagccac   1020
```

-continued

```
cccccgctgc ccgccccgg gtctaccaac cacccaccta caaccgcatc atcaaccaga    1080
tctctaccaa cgagatccag agtgaccaga acctgaaggt gctgccaccc cctctgccca    1140
ctatgcccac tctcaccagc ctcccatctt ccaccgacaa gccgtcgggc ccatggagag    1200
actgcctgca ggcccggag gatggccacg acaccagctc catctacctg gtgaagccgg    1260
agaacaccaa ccgcctcatg caggtgtggt gcgaccagag acacgacccc ggggctggaa   1320
ccgtcatcca gagacgcctg gatggctctg ttaacttctt caggaactgg gagacgtaca   1380
agcaagggtt tgggaacatt gacggcgaat actggctggg cctggagaac atttactggc   1440
tgacgaacca aggcaactac aaactcctgg tgaccatgga ggactggtcc ggccgcaaag   1500
tctttgcaga atacgccagt ttccgcctgg aacctgagag cgagtattat aagctgcggc   1560
tggggcgcta ccatggcaat gcgggtgact cctttacatg gcacaacggc aagcagttca   1620
ccaccctgga cagagatcat gatgtctaca caggaaactg tgcccactac cagaagggag   1680
gctggtggta taacgcctgt gcccactcca acctcaacgg ggtctggtac cgcgggggcc   1740
attaccggag ccgctaccag gacggagtct actgggctga gttccgagga ggctcttact   1800
cactcaagaa agtggtgatg atgatccgac cgaaccccaa caccttccac taagccagct   1860 cccctcctg acctctcgtg gccattgcca ggagcccacc ctggtcacgc tggccacagc    1920
acaaagaaca actcctcacc agttcatcct gaggctggga ggaccgggat gctggattct    1980 gtttccgaa gtcactgcag cggatgatgg aactgaatcg atacggtgtt ttctgtccct    2040
cctactttcc ttcacaccag acagcccctc atgtctccag acaggacag gactacagac     2100 aactctttct ttaaataaat taagtctcta caataaaaac acaactgcaa agtaaaaaaa    2160
aaaaaaaaaa aaa                                                       2173
```

<210> SEQ ID NO 2
<211> LENGTH: 493
<212> TYPE: PRT
<213> ORGANISM: Homo sapiens

<400> SEQUENCE: 2

```
Met Arg Pro Leu Cys Val Thr Cys Trp Trp Leu Gly Leu Leu Ala Ala
  1               5                  10                  15

Met Gly Ala Val Ala Gly Gln Glu Asp Gly Phe Glu Gly Thr Glu Glu
                 20                  25                  30

Gly Ser Pro Arg Glu Phe Ile Tyr Leu Asn Arg Tyr Lys Arg Ala Gly
             35                  40                  45

Glu Ser Gln Asp Lys Cys Thr Tyr Thr Phe Ile Val Pro Gln Gln Arg
     50                  55                  60

Val Thr Gly Ala Ile Cys Val Asn Ser Lys Glu Pro Glu Val Leu Leu
 65                  70                  75                  80

Glu Asn Arg Val His Lys Gln Glu Leu Glu Leu Leu Asn Asn Glu Leu
                 85                  90                  95

Leu Lys Gln Lys Arg Gln Ile Glu Thr Leu Gln Gln Leu Val Lys Val
                100                 105                 110

Asp Gly Gly Ile Val Ser Glu Val Lys Leu Leu Arg Lys Glu Ser Arg
            115                 120                 125

Asn Met Asn Ser Arg Val Thr Gln Leu Tyr Met Gln Leu Leu His Glu
        130                 135                 140

Ile Ile Arg Lys Arg Asp Asn Ala Leu Glu Leu Ser Gln Leu Glu Asn
145                 150                 155                 160

Arg Ile Leu Asn Gln Thr Ala Asp Met Leu Gln Leu Ala Ser Lys Tyr
```

-continued

```
                165                 170                 175
Lys Asp Leu Glu His Lys Tyr Gln His Leu Ala Thr Leu Ala His Asn
            180                 185                 190

Gln Ser Glu Ile Ile Ala Gln Leu Glu His Cys Gln Arg Val Pro
        195                 200                 205

Ser Ala Arg Pro Val Pro Gln Pro Pro Ala Ala Pro Pro Arg Val
    210                 215                 220

Tyr Gln Pro Pro Thr Tyr Asn Arg Ile Ile Asn Gln Ile Ser Thr Asn
225                 230                 235                 240

Glu Ile Gln Ser Asp Gln Asn Leu Lys Val Leu Pro Pro Leu Pro
            245                 250                 255

Thr Met Pro Thr Leu Thr Ser Leu Pro Ser Ser Thr Asp Lys Pro Ser
                260                 265                 270

Gly Pro Trp Arg Asp Cys Leu Gln Ala Leu Glu Asp Gly His Asp Thr
            275                 280                 285

Ser Ser Ile Tyr Leu Val Lys Pro Glu Asn Thr Asn Arg Leu Met Gln
        290                 295                 300

Val Trp Cys Asp Gln Arg His Asp Pro Gly Gly Trp Thr Val Ile Gln
305                 310                 315                 320

Arg Arg Leu Asp Gly Ser Val Asn Phe Phe Arg Asn Trp Glu Thr Tyr
                325                 330                 335

Lys Gln Gly Phe Gly Asn Ile Asp Gly Glu Tyr Trp Leu Gly Leu Glu
            340                 345                 350

Asn Ile Tyr Trp Leu Thr Asn Gln Gly Asn Tyr Lys Leu Leu Val Thr
        355                 360                 365

Met Glu Asp Trp Ser Gly Arg Lys Val Phe Ala Glu Tyr Ala Ser Phe
    370                 375                 380

Arg Leu Glu Pro Glu Ser Glu Tyr Tyr Lys Leu Arg Leu Gly Arg Tyr
385                 390                 395                 400

His Gly Asn Ala Gly Asp Ser Phe Thr Trp His Asn Gly Lys Gln Phe
                405                 410                 415

Thr Thr Leu Asp Arg Asp His Asp Val Tyr Thr Gly Asn Cys Ala His
            420                 425                 430

Tyr Gln Lys Gly Gly Trp Trp Tyr Asn Ala Cys Ala His Ser Asn Leu
        435                 440                 445

Asn Gly Val Trp Tyr Arg Gly Gly His Tyr Arg Ser Arg Tyr Gln Asp
    450                 455                 460

Gly Val Tyr Trp Ala Glu Phe Arg Gly Gly Ser Tyr Ser Leu Lys Lys
465                 470                 475                 480

Val Val Met Met Ile Arg Pro Asn Pro Asn Thr Phe His
                485                 490
```

<210> SEQ ID NO 3
<211> LENGTH: 498
<212> TYPE: PRT
<213> ORGANISM: Homo sapiens

<400> SEQUENCE: 3

```
Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45
```

-continued

```
Glu His Asp Gly Asn Cys Arg Glu Ser Thr Thr Asp Gln Tyr Asn Thr
 50                  55                  60

Asn Ala Leu Gln Arg Asp Ala Pro His Val Glu Pro Asp Phe Ser Ser
 65                  70                  75                  80

Gln Lys Leu Gln His Leu Glu His Val Met Glu Asn Tyr Thr Gln Trp
                 85                  90                  95

Leu Gln Lys Leu Glu Asn Tyr Ile Val Glu Asn Met Lys Ser Glu Met
                100                 105                 110

Ala Gln Ile Gln Gln Asn Ala Val Gln Asn His Thr Ala Thr Met Leu
            115                 120                 125

Glu Ile Gly Thr Ser Leu Leu Ser Gln Thr Ala Glu Gln Thr Arg Lys
130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
                180                 185                 190

Leu Leu Glu His Lys Ile Leu Glu Met Glu Gly Lys His Lys Glu Glu
            195                 200                 205

Leu Asp Thr Leu Lys Glu Glu Lys Glu Asn Leu Gln Gly Leu Val Thr
210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
                260                 265                 270

Lys Gly Gly Lys Arg Glu Glu Lys Pro Phe Arg Asp Cys Ala Asp
            275                 280                 285

Val Tyr Gln Ala Gly Phe Asn Lys Ser Gly Ile Tyr Thr Ile Tyr Ile
290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
                340                 345                 350

Gly Glu Tyr Trp Leu Gly Asn Glu Phe Ile Phe Ala Ile Thr Ser Gln
            355                 360                 365

Arg Gln Tyr Met Leu Arg Ile Glu Leu Met Asp Trp Glu Gly Asn Arg
370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
                420                 425                 430

Asp Asn Cys Met Cys Lys Cys Ala Leu Met Leu Thr Gly Gly Trp Trp
            435                 440                 445

Phe Asp Ala Cys Gly Pro Ser Asn Leu Asn Gly Met Phe Tyr Thr Ala
450                 455                 460

Gly Gln Asn His Gly Lys Leu Asn Gly Ile Lys Trp His Tyr Phe Lys
```

```
                465                 470                 475                 480
Gly Pro Ser Tyr Ser Leu Arg Ser Thr Thr Met Met Ile Arg Pro Leu
                    485                 490                 495
Asp Phe

<210> SEQ ID NO 4
<211> LENGTH: 496
<212> TYPE: PRT
<213> ORGANISM: Homo sapiens

<400> SEQUENCE: 4

Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
             20                  25                  30

Gln Tyr Gln Val Gln His Gly Ser Cys Ser Tyr Thr Phe Leu Leu Pro
         35                  40                  45

Glu Met Asp Asn Cys Arg Ser Ser Ser Pro Tyr Val Ser Asn Ala
     50                  55                  60

Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
                 85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
    130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
    210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
        275                 280                 285

Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
```

```
                    340                 345                 350
Tyr Trp Leu Gly Asn Glu Phe Val Ser Gln Leu Thr Asn Gln Gln Arg
            355                 360                 365

Tyr Val Leu Lys Ile His Leu Lys Asp Trp Glu Gly Asn Glu Ala Tyr
            370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
            450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 5
<211> LENGTH: 509
<212> TYPE: PRT
<213> ORGANISM: Homo sapiens

<400> SEQUENCE: 5

Met Leu Cys Gln Pro Ala Met Leu Leu Asp Gly Leu Leu Leu Leu Ala
1               5                   10                  15

Thr Met Ala Ala Ala Gln His Arg Gly Pro Glu Ala Gly Gly His Arg
                20                  25                  30

Gln Ile His Gln Val Arg Arg Gly Gln Cys Ser Tyr Thr Phe Val Val
            35                  40                  45

Pro Glu Pro Asp Ile Cys Gln Leu Ala Pro Thr Ala Ala Pro Glu Ala
        50                  55                  60

Leu Gly Gly Ser Asn Ser Leu Gln Arg Asp Leu Pro Ala Ser Arg Leu
65                  70                  75                  80

His Leu Thr Asp Trp Arg Ala Gln Arg Ala Gln Arg Ala Gln Arg Val
                85                  90                  95

Ser Gln Leu Glu Lys Ile Leu Glu Asn Asn Thr Gln Trp Leu Leu Lys
            100                 105                 110

Leu Glu Gln Ser Ile Lys Val Asn Leu Arg Ser His Leu Val Gln Ala
            115                 120                 125

Gln Gln Asp Thr Ile Gln Asn Gln Thr Thr Thr Met Leu Ala Leu Gly
        130                 135                 140

Ala Asn Leu Met Asn Gln Thr Lys Ala Gln Thr His Lys Leu Thr Ala
145                 150                 155                 160

Val Glu Ala Gln Val Leu Asn Gln Thr Leu His Met Lys Thr Gln Met
                165                 170                 175

Leu Glu Asn Ser Leu Ser Thr Asn Lys Leu Glu Arg Gln Met Leu Met
            180                 185                 190

Gln Ser Arg Glu Leu Gln Arg Leu Gln Gly Arg Asn Arg Ala Leu Glu
            195                 200                 205

Thr Arg Leu Gln Ala Leu Glu Ala Gln His Gln Ala Gln Leu Asn Ser
        210                 215                 220
```

-continued

| Leu | Gln | Glu | Lys | Arg | Glu | Gln | Leu | His | Ser | Leu | Leu | Asp | His | Gln | Thr |
| 225 | | | | 230 | | | | 235 | | | | 240 | | | |

Gly Thr Leu Ala Asn Leu Lys His Asn Leu His Ala Leu Ser Ser Asn
        245                 250                 255

Ser Ser Ser Leu Gln Gln Gln Gln Gln Leu Thr Glu Phe Val Gln
            260                 265                 270

Arg Leu Val Arg Ile Val Ala Gln Asp Gln His Pro Val Ser Leu Lys
        275                 280                 285

Thr Pro Lys Pro Val Phe Gln Asp Cys Ala Glu Ile Lys Arg Ser Gly
    290                 295                 300

Val Asn Thr Ser Gly Val Tyr Thr Ile Tyr Glu Thr Asn Met Thr Lys
305                 310                 315                 320

Pro Leu Lys Val Phe Cys Asp Met Glu Thr Asp Gly Gly Gly Trp Thr
                325                 330                 335

Leu Ile Gln His Arg Glu Asp Gly Ser Val Asn Phe Gln Arg Thr Trp
            340                 345                 350

Glu Glu Tyr Lys Glu Gly Phe Gly Asn Val Ala Arg Glu His Trp Leu
        355                 360                 365

Gly Asn Glu Ala Val His Arg Leu Thr Ser Arg Thr Ala Tyr Leu Leu
    370                 375                 380

Arg Val Glu Leu His Asp Trp Glu Gly Arg Gln Thr Ser Ile Gln Tyr
385                 390                 395                 400

Glu Asn Phe Gln Leu Gly Ser Glu Arg Gln Arg Tyr Ser Leu Ser Val
                405                 410                 415

Asn Asp Ser Ser Ser Ala Gly Arg Lys Asn Ser Leu Ala Pro Gln
            420                 425                 430

Gly Thr Lys Phe Ser Thr Lys Asp Met Asp Asn Asp Asn Cys Met Cys
        435                 440                 445

Lys Cys Ala Gln Met Leu Ser Gly Gly Trp Trp Phe Asp Ala Cys Gly
450                 455                 460

Leu Ser Asn Leu Asn Gly Ile Tyr Tyr Ser Val His Gln His Leu His
465                 470                 475                 480

Lys Ile Asn Gly Ile Arg Trp His Tyr Phe Arg Gly Pro Ser Tyr Ser
                485                 490                 495

Leu His Gly Thr Arg Met Met Leu Arg Pro Met Gly Ala
            500                 505

<210> SEQ ID NO 6
<211> LENGTH: 504
<212> TYPE: PRT
<213> ORGANISM: Homo sapiens

<400> SEQUENCE: 6

Asn Leu Ser Gln Leu Ala Met Leu Gln Gly Ser Leu Leu Leu Val Val
1               5                   10                  15

Ala Thr Met Ser Val Ala Gln Thr Arg Gln Glu Ala Asp Arg Gly
            20                  25                  30

Cys Glu Thr Leu Val Val Gln His Gly His Cys Ser Tyr Thr Phe Leu
        35                  40                  45

Leu Pro Lys Ser Glu Pro Cys Pro Pro Gly Pro Glu Val Ser Arg Asp
    50                  55                  60

Ser Asn Thr Leu Gln Arg Glu Ser Leu Ala Asn Pro Leu His Leu Gly
65                  70                  75                  80

Lys Leu Pro Thr Gln Gln Val Lys Gln Leu Glu Gln Ala Leu Gln Asn
                85                  90                  95

-continued

```
Asn Thr Gln Val Leu Lys Lys Leu Glu Arg Ala Ile Lys Thr Ile Leu
                100                 105                 110

Arg Ser Lys Leu Glu Gln Val Gln Gln Gln Met Ala Gln Asn Gln Thr
            115                 120                 125

Ala Pro Met Leu Glu Leu Gly Thr Ser Leu Leu Asn Gln Thr Thr Ala
        130                 135                 140

Gln Ile Arg Lys Leu Thr Asp Met Glu Ala Gln Leu Leu Asn Gln Thr
145                 150                 155                 160

Ser Arg Met Asp Ala Gln Met Pro Glu Thr Phe Leu Ser Thr Asn Lys
                165                 170                 175

Leu Glu Asn Gln Leu Leu Leu Gln Arg Gln Lys Leu Gln Gln Leu Gln
            180                 185                 190

Gly Gln Asn Ser Ala Leu Glu Lys Arg Leu Gln Ala Leu Glu Thr Lys
        195                 200                 205

Gln Gln Glu Glu Leu Ala Ser Glu Leu Ser Lys Lys Ala Lys Leu Leu
210                 215                 220

Asn Thr Leu Ser Arg Gln Ser Ala Ala Leu Thr Asn Glu Glu Arg Gly
225                 230                 235                 240

Leu Arg Gly Val Arg His Asn Ser Ser Leu Leu Gln Asp Gln Gln His
                245                 250                 255

Ser Leu Arg Gln Leu Leu Val Leu Leu Arg His Leu Val Gln Glu Arg
            260                 265                 270

Ala Asn Ala Ser Ala Pro Ala Phe Ile Met Ala Gly Glu Gln Val Phe
        275                 280                 285

Gln Asp Cys Ala Glu Ile Gln Arg Ser Gly Ala Ser Ala Ser Gly Phe
290                 295                 300

Tyr Thr Ile Gln Val Ser Asn Ala Thr Lys Pro Arg Lys Val Phe Cys
305                 310                 315                 320

Asp Leu Gln Ser Ser Gly Gly Arg Val Thr Leu Ile Gln Arg Arg Glu
                325                 330                 335

Asn Gly Thr Val Asn Phe Gln Arg Asn Val Lys Asp Tyr Lys Gln Gly
            340                 345                 350

Phe Gly Asp Pro Ala Gly Glu His Val Glu Leu Gly Asn Glu Val Val
        355                 360                 365

His Gln Leu Thr Arg Arg Ala Ala Tyr Ser Leu Arg Val Glu Leu Gln
370                 375                 380

Asp Val Glu Gly His Glu Ala Tyr Ala Gln Tyr Glu His Phe His Leu
385                 390                 395                 400

Gly Ser Glu Asn Gln Leu Tyr Arg Leu Ser Val Val Gly Tyr Ser Gly
                405                 410                 415

Ser Ala Gly Arg Gln Ser Ser Leu Val Leu Gln Asn Thr Ser Phe Ser
            420                 425                 430

Thr Leu Asp Ser Asp Asn Asp His Cys Leu Cys Lys Cys Ala Gln Val
        435                 440                 445

Met Ser Gly Gly Trp Trp Phe Asp Ala Cys Gly Leu Ser Asn Leu Asn
450                 455                 460

Asp Val Tyr Tyr His Ala Pro Asp Asn Lys Tyr Lys Met Asp Gly Glu
465                 470                 475                 480

Arg Val His Tyr Phe Lys Gly Pro Ser Tyr Ser Leu Arg Ala Ser Arg
                485                 490                 495

Met Met Glu Arg Pro Leu Asp Glu
            500
```

```
<210> SEQ ID NO 7
<211> LENGTH: 28
<212> TYPE: DNA
<213> ORGANISM: Homo sapiens

<400> SEQUENCE: 7
gcgaattcac catgaggcca ctgtgcgt                                              28

<210> SEQ ID NO 8
<211> LENGTH: 29
<212> TYPE: DNA
<213> ORGANISM: Homo sapiens

<400> SEQUENCE: 8
ggaagcttat ggaaggtgtt ggggttcgg                                             29
```